United States Patent [19]

Sanders et al.

[11] Patent Number: 5,232,833
[45] Date of Patent: Aug. 3, 1993

[54] ACCUMULATION OF HEAT SHOCK PROTEINS FOR EVALUATING BIOLOGICAL DAMAGE DUE TO CHRONIC EXPOSURE OF AN ORGANISM TO SUBLETHAL LEVELS OF POLLUTANTS

[75] Inventors: Brenda M. Sanders; Kenneth D. Jenkins, both of Long Beach, Calif.; Jack L. Nichols, Vancouver; Bryan E. Imber, Victoria, both of Canada

[73] Assignee: Stressgen Biotechnologies Corporation, Canada

[21] Appl. No.: 404,401

[22] Filed: Sep. 12, 1989

Related U.S. Application Data

[63] Continuation-in-part of Ser. No. 244,757, Sep. 14, 1988, abandoned.

[51] Int. Cl.[5] .................... C12Q 1/00; G01N 33/53
[52] U.S. Cl. .................................. 435/7.21; 435/7.2; 435/7.22; 435/7.31; 435/7.32; 435/29
[58] Field of Search ............... 435/29, 7.2, 7.21, 7.22, 435/7.31, 7.32

[56] References Cited

U.S. PATENT DOCUMENTS

| | | | |
|---|---|---|---|
| 4,582,788 | 4/1986 | Erlich | 435/6 |
| 4,758,512 | 7/1988 | Goldberg et al. | 435/68 |
| 4,797,359 | 1/1989 | Finkelstein | 435/68 |

OTHER PUBLICATIONS

Deshaies, R. J., et al., "A subfamily of stress proteins facilitates translocation of secretory mitochondrial precursor polypeptides," *Nature*, 332:800–805 (1988).
Bardwell, J. C. A., et al., "Major heat shock gene of Drosophila and the *Escherichia coli* heat-inducible dnaK gene are homologous," Proc. Natl. Acad. Sci. USA, 81:848–852 (1984).
Greenberg, S. G., "Comparison of Labeled Heat Shock Proteins in Neuronal and Non-neuronal Cells of *Aplysia californica*," *The Journal of Neuroscience*, 5:1239–1245 (1985).
Catelli, M. G. et al., "Cloning of the chick hsp 90 cDNA in expression vector," *Nucleic Acids Research*, 13:6035–6047 (1985).
Cheng, M. Y., et al., "Mitochondrial heat-shock protein hsp60 is essential for assembly of proteins imported into yeast mitochondria," *Nature*, 337:620–625 (1989).
Catelli, M. G., et al., "The common 90-kd protein component of non-transformed '8S' steroid receptors is a heat-shock protein," *The EMBO Journal*, 4:3131–3135 (1985).

(List continued on next page.)

Primary Examiner—Sam Rosen
Attorney, Agent, or Firm—Seed and Berry

[57] ABSTRACT

Method of detecting chronic exposure of an organism to a pollutant, and for evaluating biological damage due to chronic exposure to sublethal levels of pollutants and kits for carrying out the method are disclosed. The methods comprise:

(a) sampling at least one organism in order to determine whether it has been chronically exposed to a sublethal concentration of one or more pollutants in its environment, under sampling conditions that do not induce any additional heat shock protein (hsp) response in the organism;

(b) obtaining a sample of cells or secretions of said organism, suspected of having elevated levels of heat shock proteins and solubilizing the heat shock proteins in the sample; and (c) measuring the concentration of a heat shock protein selected from hsp 70, hsp 60 and ubiquitin, in said sample.

The invention also provides methods for evaluating biological damage due to chronic exposure of the organism by the above method and then comparing the measured concentration of hsp to a predetermined standard calibration curve which correlates hsp concentration with physiological impairment of growth or reproductive processes, and kits for carrying out the methods.

13 Claims, 7 Drawing Sheets

OTHER PUBLICATIONS

Irby, R. B., et al., "Stress Protein Synthesis in Responseto Toxicant Exposure in Two Species of Rotifer," ASTM Symposium on Aq. Tax., Apr. 18, 1989.

Chappell, T. G. et al., "Uncoating ATPase Is a Member of the 70 Kilodalton Family of Stress Proteins," *Cell*, 45:3–13 (1986).

Cochrane, B. J., et al., "Stress Proteins and Toxicant Stress in Rotifers,", SETAC, Nov. 15, 1988.

Dragon, E. A., et al., "The Genome of *Trypanosoma cruzi* Contains a Constitutively Expressed, Tandemly Arranged Multicopy Gene Homologous to a Major Heat Shock Protein," *Molecular and Cellular Biology*, 7:1271–1275 (1987).

Jenkins, K. D., et al., "Cytosolic Metal Distribution as an Indicator of Toxicity in Sea Urchins from the Southern California Bight," *Marine Pollution Bulletin*, 13:413–421 (1982).

Dworniczak, B., et al., "Structure and expression of a human gene coding for a 71 kd heat shock 'cognate' protein," *Nucleic Acids Research*, 15:5181–5197 (1987).

Jenkins, K. D., et al., "Determining the Biological Significance of Contaminant Bioaccumulation," *Concepts in Marine Pollution Measurements*, ed. H. H. White.

Farrelly, F. W., et al., "Complete Sequence of the Heat Shock-inducible HS90 Gene of *Saccharomyces cerevisiae*," *The Journal of Biological Chemistry*, 259:5745–5751 (1984).

Caltabiano, M. M., et al., "Induction of 32- and 34-kDa Stress Proteins by Sodium Arsenite, Heavy Metals, and Thiol-reactive Agents," *Journal of Biological Chemistry*, (1986).

Glass, D. J., et al., "Conserved Sequences and Transcription of the hsp70 Gene Family in *Trypanosoma brucei*," *Molecular and Cellular Biology*, 6:4657–4666 (1986).

Roman, H. L., et al., Eds., *Annual Review of Genetics*, 18:296–329 (1984).

Heikkila, J. J., et al., "Expression of a Set of Fish Genes Following Heat or Metal Ion Exposure," *The Journal of Biological Chemistry*, 257:12000–12005 (1982).

Kee, S. C., P. S. Noble. "Concomitant Changes in High Temperature Tolerance and Heat-Shock Proteins in Desert Succulents," *Plant Physiol.* 80:596–598 (1986).

Ingolia, T. D., et al., "Drosophila gene related to the major heat shock-induced gene is transcribed at normal temperatures and not induced by heat shock," *Proc. Natl. Acad. Sci, USA*, 79:525–529 (1982).

Landry, J., et al., "Synthesis and Degradation of Heat Shock Proteins during Development and Decay of Thermotolerance," *Cancer Res.* 42:2457–2461 (1982).

Ingolia, T. D., et al., "*Saccharomyces cerevisiae* Contains a Complex Multigene Family Related to the Major Heat Shock-Inducible Gene of Drosophila," *Molecular and Cellular Biology*, 2:1388–1398 (1982).

Mosser, D. D., et al., "Induction and Decay of Thermotolerance in Rainbow Trout Fibroblasts," *J. Cell. Physiol.* 132:155–160 (1987).

Kelley, P. M., et al., "Antibodies to Two Major Chicken Heat Shock Proteins Cross-React with Similar Proteins in Widely Divergent Species," *Molecular and Cellular Biology*, 2:267–274 (1982).

Sanders, B. M., list of invited seminars.

Kothary, R. K., et al., "70-Kilodalton Heat Shock Polypeptides from Rainbow Trout: Characterization of cDNA Sequences," *Molecular and Cellular Biology*, 4:1785–1791 (1984).

U.S. Ser. No. 931,991 by Welch filed Nov. 18, 1986, now abandoned.

Lowe, D. G., et al., "Mouse and Drosophila Genes Encoding the Major Heat Shock Protein (hsp70) Are Highly Conserved," *Molecular and Cellular Biology*, 3:1540–1543 (1983).

Burns, C. Patrick, et al., "Influence of Rate of Heating on Thermosensitivity of L1210 Leukemia: Membrane Lipids and $M_r$ 70,000 Heat Shock Protein," *Cancer Research*, 46:1882–1887 (Apr. 1986).

Lowe, D. G., et al., "Proteins related to the mouse L-cell major heat shock protein are synthesized in the absence of heat shock gene expression," *Proc. Natl. Acad. Sci. USA*, 81:2317–2321 (1984).

Jaattela, M., et al., "Heat Shock Protects WEHI-164 Target Cells From the Cytolysis by Tumor Necrosis Factors $\alpha$ and $\beta$," *Eur. J. Immunol.*, 19:1413–1417 (1989).

Moran, L. A., et al., "The major heat-shock protein (hsp70) gene family: related sequences in mouse, Drosophila, and yeast," *Can. J. Biochem. Cell Biol.*, 61:488–499 (1983).

United States International Searching Authority,

OTHER PUBLICATIONS

Search Report, date of mailing: 16 Jan. 1990.

Munro, S., ete al., "An Hsp70-like Protein in the ER: Identity with the 78 kd Glucose-Regulated Protein and Immunoglobulin Heavy Chain Binding Protein," *Cell*, 46:291–300 (1986).

Rebbe, N. F., et al., "Nucleotide sequence of a cDNA for a member of the human 90-kDa heat-shock protein family," *Cell*, 53:235–245 (1987).

Sanchez, E. R., et al., "Evidence That the 90-kDa Phosphoprotein Associated with the Ultransformed L-cell Gluccorticoid Receptor is a Murine Heat Shock Protein," *The Journal of Biological Chemistry*, 260:12398–12401 (1985).

Southgate, R., et al., "Organization, Sequences, and Induction of Heat Shock Genes," *Changes in Eukaryotic Gene Expression in Response to Environmental Stress*, Academic Press, San Diego, pp. 3–30 (1985).

Subjeck, J. R., et al., "Association between the Mammalian 110,000-dalton Heat-shock Protein and Nucleoli," *The Journal of Cell Biology*, 97:1389–1395 (1983).

Torok, I., et al., "Nucleotide sequences of heat shock activated genes in Drosophila melanogaster. I. Sequences in the regions of the 5' and 3' ends of the hsp 70 gene in the hybrid plasmid 56H8," *Nucleic Acids Research*, 8:3105–3123 (1980).

Torok, I., et al., "Extensive Regions of Homology Associated with Heat-induced Genes at Loci 87A7 and 87C1 in *Drosophila melanogaster*," pp. 19–25.

Velazquez, J. M., et al., "hsp70: Nuclear Concentration During Environmental Stress and Cytoplasmic Storage During Recovery," *Cell*, 36:655–662 (1984).

Voellmy, R., et al., "Isolation and functional analysis of a human 70,000-dalton heat shock protein gene segment," *Proc. Natl. Acad. Sci. USA*, 82:4949–4953 (1985).

Welch, W. J., et al., "Nuclear and Nucleolar Localization of the 72,000-dalton Heat Shock Protein in Heat--shocked Mammalian Cells," *The Journal of Biological Chemistry*, 259:4511–4513 (1984).

Widelitz, R. B., et al., "Effects of Cycloheximide on Thermotolerance Expression, Heat Shock Protein Synthesis, and Heat Shock Protein mRNA Accumulation in Rat Fibroblasts," *Molecular and Cellular Biology*, 6:1088–1094 (1986).

Wu, B., et al., "Structure and Expression of the Human Gene Encoding Major Heat Shock Protein HSP70," *Molecular and Cellular Biology*, 5:330–341 (1985).

Sanders, B. M., "The Role of the Stress Proteins Response in Physiological Adaptation of Marine Molluscs," *Marine Environmental Research*, 24:207–210 (1988).

Miller, S. G., "Association of a Sperm-Specific Protein with the Mitochondrial $F_1F_0$-ATPase in Heliothis: Implications for Sterility of *H. Virescens* x H. Subflexa Backcross Hybrids," *Insect Biochem.*, 17:417–432 (1987).

Sanders, B. M., et al., "Free Cupric Ion Activity in Seawater: Effects on Metallothionein and Growth in Crab Larvae," *Science*, 222:53–55 (1983).

Sanders, B. .M., et al., "Relationships between Free Cupric Ion Concentrations in Sea Water and Copper Metabolism and Growth in Crab Larvae," *Biol. Bull.* 167:704–712 (1984).

Roch, M., "Hepatic Metallothionein in Rainbow Trout (*Salmo gairdneri*) as an Indicator of Metal Pollution in the Campbell River System," *Can. J. Fish. Aquat. Sci.*, 39:1596–1601 (1982).

Jenkins, K. D., et al., "Contaminants in White Croakers *Genyonemus Lineatus* (Ayres, 1855) from the Southern California Bight: I. Trace Metal Detoxification/Toxification," *Psychological Mechanisms of Marine Pollutant Toxicity*, W. B. Vernberg et al., eds., Academic Press, Inc., 1982.

Jenkins, K. D., et al., "Relationships between Free Cadmium Ion Acitivty in Seawater, Cadmium Accumulation and Subcellular Distribution, and Growth in Polychaetes," *Environmental Health Perspectives*, 65:205–210 (1986).

Roch, M., et al., "Hepatic Metallothionein Production and Resistance to Heavy Metals by Rainbow Trout (*Salmo gairdneri*)-II." Held in a Series of Contaminated Lakes, Comp. Biochem. Physiol. 77C:77–82 (1984).

Jenkins, K. D., "Metal Regulation and Toxicity in Aquatic Organisms," *Mechanism of Drug Action*, Academic Press, Inc., 1983.

Xiao, H., et al., "Germline Transformation Used to Define Key Features of Heat-Shock Response Elements", *Science*, 239:1139–1142 (1988).

Sanders, B. M., "The Stress Proteins Response: A Novel Monitoring Technique".

Reading, D. S., et al., "Characterization of the yeast HSP60 gene coding for a mitochondrial assembly factor," *Nature*, 337:655–659 (1989).

Fig. 9.

Cu TBT HS C

ACCUMULATION OF HEAT SHOCK PROTEINS FOR EVALUATING BIOLOGICAL DAMAGE DUE TO CHRONIC EXPOSURE OF AN ORGANISM TO SUBLETHAL LEVELS OF POLLUTANTS

This is a continuation-in-part of U.S. Ser. No. 244,757, filed Sep. 14, 1988, now abandoned.

FIELD OF THE INVENTION

This invention relates to methods for evaluating environmental stress and associated biological damage. In particular, the invention relates to assays for detecting increases in levels of heat shock proteins (hsp's) which are associated with chronic exposure of organisms to environmental pollutants. The present invention also relates to a method for correlating the amount of heat shock (hs) protein produced with physiological impairment of growth or reproductive processes of the organism. In yet another aspect, it relates to assay kits for carrying out the method of the present invention.

BACKGROUND OF THE INVENTION

Developments in two separate areas of research may be of interest. The first area relates to methods of monitoring the impact of contaminants on the environment. In a second and separate area of technology, molecular biologists have investigated the genetic regulation of peptide synthesis, utilizing as a model the hs response of a variety of species.

In the first area of research, several kinds of approaches have been used to monitor the impacts of man's activities on the environment. Environmental monitoring has most often focused on evaluating the fate of contaminants through exhaustive chemical analysis of sediment, water, and tissue samples to determine the degree of anthropogenic inputs at a particular site. Correlations have been found between levels of contaminants and the degree of industrial activities in surrounding areas; however, this approach is extremely expensive and gives little insight concerning the effects of these contaminants on organisms in the ecosystem.

In an attempt to address the issue of biological effects, the Environmental Protection Agency ("EPA") has developed water quality criteria that provide a basis for estimating the relative toxicity of each pollutant. In this approach, laboratory bioassay data is obtained for each chemical, and an elaborate procedure is used to derive a criterion number for each chemical that would hypothetically protect organisms in the actual field environment. Although extrapolating from the laboratory to the field has questionable validity, this process does provide a concentration for each pollutant against which the chemical data obtained from a site can be compared. The development of a separate criterion number for each pollutant, however, is a time-consuming and expensive process and is not practical for the over 20,000 pollutants estimated by the EPA to be impacting our waters. This chemical-by-chemical approach also does not take into account the complex interactions that may occur in the complex mixtures of pollutants normally found in the real world.

Because of these problems, the EPA has begun to use short-term bioassays to assess the relative toxicity of complex effluents and surface waters. Gradually, these tests are carried out in the laboratory with a standard organism, such as the fat head minnow or daphnia. The results of these tests tend to be variable, and it is difficult to relate observed toxicity to the presence of pollutants in the test water, let along individual pollutants in a complex mixture. A major problem with these bioassays, as well as with other bioassays, is that it is difficult to extrapolate from laboratory tests to the actual conditions encountered by indigenous organisms in the field.

In another approach, it has bee noted that contaminant-induced stress responses have been observed at every level of biological organization. Initially, contaminants interact with biological systems at the molecular level. These interactions may result in physiological perturbations at the cellular and organismal levels. These perturbations can, in turn, result in effects that have significance at the population and community levels, such as reductions in reproduction, growth, and survival. The time period for expression of toxic effects at the community level is highly variable; it may be on the order of years. Alternatively, where community stability is regulated by one of several "keystone species," subtle stress-induced changes in the reproductive success of these species may be profound, with correspondingly rapid effects on the community and population.

The variations in response time from initial molecular impacts to population and community effects often make it difficult to link inputs of sublethal concentrations of contaminants with perturbations at these higher levels of organization. These problems are further compounded by the natural variability in community structure and productivity that are difficult to differentiate from contaminant-induced changes. For these reasons, cause and effect relationships between contaminant action and biological responses can best be established by examining the mechanisms of contaminant impact with individual organisms. The data can then be related to population and community impacts.

Accordingly, another approach to monitoring involves an initial screening of field sites to determine whether organisms are adversely impacted in situ. With this strategy, one can systematically follow a series of biological and chemical procedures arranged in hierarchical order with appropriate feedback loops to evaluate the extent of impact of stress at the organismal level. The final step involves the identification of specific contaminants that may be the causative agents. This monitoring strategy strives to evaluate, in situ, general stress in the organism and to delineate the specific factors that are involved in a systematic and cost effective fashion. Evaluating stress in native organisms in situ is important because the effect of each environmental variable is dependent on all other variables encountered by the organism. Although organisms may be exposed to a wide range of environmental stressors at any given time, they have only a finite capacity to adapt. Therefore, they integrate the effects of each variable into a total stress load. The effects of subsequent environmental changes will ultimately depend upon the overall exposure history of the organism.

Organisms use many strategies to minimize detrimental effects of environmental changes: they elicit avoidance responses, evoke repair or stabilization mechanisms, and synthesize detoxication enzymes or binding ligands. All of these processes require energy, which is diverted from other cellular processes. As the stress load increases, there will be a threshold at which this diversion disturbs important processes such as growth and reproduction. Thus, perturbations in growth and reproduction have been used as an indicator of stress and are described in Widdows in *Mar. Poll. Bull.*, 16:129-134 (1985). Other types of monitoring techniques that are currently being used as indicators of stress at the organismal level include: scope for growth (Warren and Davis, The Biological Basis of Freshwater Fish Production, *Blackwell Scientific,* Oxford, pp. 175-214, (1975)), growth inhibition (Sanders and Jenkins, *Bio. Bull.,* 167:704-712 (1984)), and perturbations in the regulation of growth and hormesis (Stebbing, *J. Mar. Biol. Assay U.K.,* 61:35-63 (1981a); Laughlin, *Science,* 211:705-705 (1981); Sanders, *Crustacean Issues,* Vol. 2: Crustacean Growth, Ed Wenner, Balkema Press (1985)). However, these techniques are of limited use because: (1) they are not based on the mechanisms that underlie the relationship between general stress physiology and toxicity and, thus, measure stress indirectly; (2) they lack the sensitivity of cellular level parameters; and, (3) they cannot be used conveniently to measure stress in native organisms exposed in situ.

A tiered approach for monitoring biological damage due to contaminant exposure which is rapid and relatively inexpensive would be a major improvement in the state of the art. In this tiered initial screening (tier I) would evaluate the organism's integrated "stress load" as an index of general stress. Negative results at this stage would indicate the organism was not stressed and further testing would be unnecessary. A positive result would require identification of the causation agents. Tier II assays would be undertaken to identify exposure to specific pollutants.

One such approach for identifying the nature of the stressor has been measuring the concentrations of total contaminants in tissues of stressed organisms. However, the relationships between contaminant concentration in organism tissue and toxic effects are complex and difficult to establish because organisms have specific metabolic mechanisms that modify, sequester, compartmentalize, and excrete contaminants. The potential toxicity of a contaminant will depend upon both the amount that has been accumulated and how effectively the organism can metabolize it.

Traditional whole organism techniques for evaluating stress (e.g., growth and reproduction studies) are expensive, time-consuming, and difficult to apply in the field. In addition, these techniques are often organism-specific and cannot easily be applied to a range of localities. As a result of these limitations, a number of biochemical assays have been and are being developed to address this issue.

Most of the biochemical approaches in current use are contaminant-specific in that they only respond to specific class on contaminants (tier II approaches) and, thus, are not useful indicators of general stress. Stressor-specific assays include: (1) the cholinesterase assay in which the activity of the enzyme cholinesterase is used to screen for exposure to organophosphate or carbamate compounds; (2) the mixed function oxidase enzyme (MFO) assay in which induction of synthesis of isoforms of MFOs are used as an indicator of exposure to xenobiotic compounds, including aromatic hydrocarbons and halogenated biphenyls; and, (3) the induction of synthesis and accumulation of metals on the protein, metallothionein, which serves as an indicator of metal exposure.

Not only is each of these methods limited as to the types of contaminants it responds to, but they deal only with exposure and do not necessarily assess the level of stress the organism is experiencing as a consequence of that exposure. Only two biochemical methods are now in use as nonspecific indicators of stress (tier I). One depends upon measuring RNA/DNA ratios that reflect shifts between cell division (DNA synthesis) and non-division (RNA synthesis) events. The other method makes use of taurine/glycine ratios which reflect metabolic shifts. Both of these ratios are indirect measures of stress, vary in response to metabolic changes that are not stress related, and have not proven useful as sensitive general stress indices.

In view of these shortcomings, the limitations of prior art procedures for evaluating environmental stress are readily apparent. In summary, the prior techniques for addressing environmental stress are all indirect in nature and thus provide ambiguous results. The four major techniques are: (1) direct chemical determinations of contaminants in the environment, (2) total concentration of chemical constituents in tissues of organisms collected from the environment, (3) biological surveys of population and community structures, and, (4) physiological monitoring in laboratory bioassays. Direct chemical measurements in the environment are very expensive and provide limited insight into biological effects of those chemicals on organisms. Measurements of chemical constituents in tissues of organisms correlate poorly with general physiological stress. The high degree of natural variability in biological populations and communities makes it difficult, if not impossible, to establish cause and effect relationships between contaminant exposure and community stress. Laboratory bioassays are usually conducted on single organisms and are limited to individual chemical stressors. They are cumbersome and expensive and do not realistically reflect the complex contaminant mixtures normally encountered in the natural environment.

Accordingly, there is a need for sensitive, rapid, and direct methods for evaluating the total stress load in organisms exposed in the laboratory and in situ. In particular, what is required is a simple and inexpensive field technique that can specifically evaluate the integrated stress load of indigenous organisms and thereby monitor adverse biological effects from contaminant exposure.

The second area of background technology relates to heat shock proteins. These proteins are commonly referred to as heat-shock proteins (hsp's) or heat-stress proteins since it was under conditions of hyperthermia that their synthesis was first observed.

The hsp's are induced by a wide variety of environmental conditions including high levels of heavy metals (Hammond, G. L., Y. K. Lai, C. L. Market, *Proc. Natl. Acad. Sci.* U.S.A. 79:3485-3488 (1982), Caltabiano, M. M., T. P. Koestler, G. Poste, R. G. Greig, *J. Biol. Chem.* 261:13381-13386 (1986)), xenobiotics (Irby, R. B., T. W. Snell, B. J. Cochrane, submitted), oxidative compounds (Kapoor, M., J. Lewis, *Can. J. Microbiol.* 33:162-168 (1987), teratogens (Bournias-Vardiabasis, N., R. L. Teplitz, G. F. Chernoff, R. L. Seecof., *Teratology* 28:109-122 (1983), Bournias-Vardiabasis, N., C. H. Buzin, *Teratogen. Carcinogen. Mutagen.* 6:523-536 (1986)), hepatocarcinogens (Carr, B. I., T. H. Huang, C. H. Buzin, K. Itakura, *Cancer Res.* 46:5106-5111 (1986), anoxia (Spector, M. P., Z. Aliabadi, T. Gonzalez, J. W. Foster, *J. Bacteriol.* 168:420-424 (1986), and fluctuations in salinity (Ramagopal, S., *Plant Physiol.* 84:324-331 (1987)).

The heat shock protein response has been observed in bacteria, yeast, plants, Dictyostelium, Tetrahymena, fruit flies, nematodes, chickens, rats, mice, and humans. The response, in fact, has been observed in every species examined to date and, in the case of higher eukaryotes, is not restricted to a particular tissue. See, for example, Neidhardt, *Ann. Rev. Genet.*, 18:295-329 (1984).

Although the number of hsp's induced by heat shock and their exact size are both tissue and species specific, five "universal" hsp's are found in all eukaryotes. Four of these are referred to by their apparent molecular weight on SDS-polyacrylamide gels: hsp 90, hsp 70, hsp 58 and the low molecular weight hsp 20-30. The fifth hsp is an 8 kDa protein called ubiquitin. In eukaryotes each hsp is comprised of a multigene family, the members of which are regulated by different promoters and code for closely related protein isoforms (Lindquist, S., *Ann. Rev. Biochem.* 55:1151-1191 (1986, Schlesinger, M. J., *J. Cell. Biol.* 103:321-325 (1986), Schlesinger, M. J., *Atlas of Sci. Biochem.* 161-164 (1988)). Most of these proteins are synthesized at high levels in stressed cells. However, with the exception of the 72 kDa protein, a highly inducible member of the hsp 70 family, all of these proteins are also present in much lower concentrations in unstressed cells. The initial observations that many hsp's are found in "normal" cells and that hsp 20-30 are developmentally induced in larval systems lead to the suggestion early on that hsp's play a role in normal cellular activities.

Collectively the hsp's appear to be involved in the protection, enhanced survival and restoration of normal cellular activities in stressed cells (Subject, J. R., T.-T. Shyy., *Cell. Physiol.* 19:C1-C17 (1986). The induction of hsp's by a mild heat shock enhances the tolerance of the cell to subsequent, more severe heat shock, a phenomenon often referred to as thermotolerance or when other environmental conditions are involved "acquired tolerance" (Dean, R. L., B. G. Atkinson, Can. *J. Biochem. Cell Biol.* 61:472-492 (1982), Landry, J., Bernier, D., Chretien, P., Nicole, L. M., Tanguay, R. M., Marceau, N., *Cancer Res.* 42:2457-2461 (1982), Berger, H. M., M. P. Woodward, *Exp. Cell Res.* 147:437-442 (1983), Stephanous, G., S. N. Alahiotis, C. Christogoulou, V. J. Marmaras, *Devel. Genet.* 299-308 (1983), Roberts, P. B., *Int. J. Radiat. Biol.* 45:27-31 (1984), Mirkes, P. E., *Dev. Biol.* 119:115-122 (1987). The induction, expression and decay of acquired tolerance correlates with the induction, accumulation and degradation of heat shock proteins (Landry, J., Bernier, D., Chretien, P., Nicole, L. M., Tanguay, R. M., Marceau, N., *Cancer Res.* 42:2457-2461 (1982), Subject, J. R., J. Sciandra, R. J., Johnson, Br. *J. Radiol* 55:579-584 (1983), Nickells R. W., L. W. Browder, *Dev. Biol.* 112:391-395 (1985), Tomasovic, S. P., T. M. Koval, *Int. J. Radiat. Biol.* 48:635-650 (1985), Mosser, D. D., J. van Oostrom, N. C. Bols., *J. Cell. Physiol.* 132:155-160 (1987), Mosser, D. D., N. C. Bols., *J. Comp. Physiol. B.* 158 (1988).

Upon exposure to a stressor, three distinct events result in a rapid change in metabolic activities within the cell: (1) there is increased transcription of heat shock peptide mRNAs, which are then preferentially translocated to the cytoplasm; (2) the transcription of most other mRNAs is suppressed; and (3) the normal translational activities of the ribosomes are disrupted so that hsp's are preferentially translated. The overall result of these events is that the cell rapidly begins synthesizing hsp's and synthesis of other peptides is repressed. No new peptides or RNA synthesis is necessary to activate the transcription of the heat shock peptide genes, indicating that preexisting factors may be involved. Cell type, state of cell differentiation, type of stressor, and the duration and intensity of stress can affect the quantity and quality of a particular suite of hsp's.

Only very recently have cell biologists begun to understand the molecular mechanisms underlying the physiology of stressed cells. Welch, W. J., J. P. Suhan, *J. Cell Biol.* 103:2035-2053 (1986). Serious attention to this important cellular phenomena has occurred largely because of the discovery that all cells dramatically alter their gene expression in response to changes in environmental conditions. This alteration in transcriptional activity, referred to as the heat shock response (hsr), appears to be an attempt to protect the cell from damage and to repair existing damage. Schlesinger, M. J., M. Ashburner, A. Tissieres, cold Spring Harbor, N.Y.: Cold Spring Harbor Laboratory, pp. 1-440 (1982). Changes in gene expression associated with the hsr are extremely rapid and result in the induced synthesis and accumulation of heat shock proteins. Most hsp's are found in low concentrations in all cells where they play a role in normal cellular function. Although the induction of some of these hsp's is independent of the nature of the stressor, while others are quite stressor specific. These experiments have all dealt with environmentally unrealistic stress or conditions; i.e., conditions unlikely to occur in the environment.

Unfortunately, to date little is known about the environmental relevance of the stress response and much research needs to be focused in this area. Much of the research on the hsr has involved exposure of cells in culture to perturbations which are often extreme and unlikely to occur naturally in the environment (Krause, K. W., E. M. Hallberg, R. L. Hallberg, *Molec. Cell. Biol.* 6:3854-3861 (1986), Heuss-LaRosa, K., R. R. Mayer, J. H. Cherry, *Plant Physiol.* 85:4-7 (1987), Welch, W. J., L. A. Mizzen, *J. Cell Biol.* 106:1117-1130 (1988).

Although the heat shock response is well documented in the literature, the work in this area is being conducted by molecular biologists whose principal focus is using the hsr to address basic molecular genetics questions; e.g., the regulation of gene expression. Much of the work focuses on developing and understanding how genes are regulated in eukaryotes. For example, a recent article by Xiao et al., *Science,* 239:1139-1142 (1988) describes heat shock gene regulation and concludes that through a determination of what turns on the heat shock gene, it may be possible to design better expression vectors for producing large amounts of desired gene products in eukaryotes. Additional work has focused on the molecular mechanisms of heat shock function in the cell. Antibodies and gene probes for hsp's have been used by molecular biologists to isolate hsp specific clones from gene libraries of various species, to characterize the genetic organization of the heat shock genes, and to study hsp regulation and function. In short, prior use of gene probes and antibodies has been focused on basic research in molecular biology and not on developing assay methods for evaluating biological damage caused by environmental contamination.

The technique most frequently used involves metabolic labeling wherein tissues are incubated with an amino acid tagged with a radioisotope (i.e. $^{35}$S, $^{14}$C, $^3$H). The tissue is then homogenized and the proteins are separated by one or two dimensional electrophoresis, and autoradiographed to examine incorporation of the radioisotope into specific proteins. This technique provides information on the entire translational profile in response to a stressor and can be particularly useful for identifying new inducible proteins. However, under continuous exposure to moderate (e.g. sublethal) stress conditions these dramatic changes in translational patterns are transient (approximately 18 hours in Mytilus exposed to a mild heat shock) and translational activity reverts to patterns similar to those found in controls. See, for example, Heikkila, J. J. et al., *J. Biol. Chem.* 257:12000–12005 (1982); Canvalho, M. and M. S. Freitas, *J. Cell. Phys.* 137:455–461 (1988); Lindquist, S., *Ann. Rev. Biochem.* 55:1151–1191 (1986); and Kapoor, M., *Int. J. Biochem*, 18:15–29 (1986). The short, transient response is followed by a rapid return to control levels of hsp synthesis. Based on these observations using metabolic labeling studies, it would not have been expected that it would not be possible to monitor biological damage to organisms exposed to contaminants in their environment by measuring hsp levels after the initial transient hsp response.

Using methods different from metabolic labelling studies to monitor hsp levels in an organism, the present inventors have surprisingly discovered that the levels of some hsp's remain relatively high in the organism even after they determine the levels of transcription and translation of the hsp's have returned back to control levels.

FIG. 1 herein depicts the type of results obtained from metabolic labeling studies which are used to measure synthetic rates.

FIG. 2 depicts the type of results observed by measuring the concentration of an hsp and its mRNA. These results are the basis of the present assay method.

Accordingly, an object of the present invention is to provide assays and kits for detecting chronic, sublethal environmental contamination by pollutants, and assays and kits for detecting biological damage at the organismal level based on correlating the concentration of heat shock proteins to physiological indices of impairment of the organism.

The manner in which these and other objects are realized by the present invention will be apparent from the summary and detailed description set forth below.

SUMMARY OF THE INVENTION

As noted above, in the past, it has been recognized that heat shock proteins could be induced by severe environmental perturbations. However, it was not appreciated that measurable increases in hsp's could be induced by environmentally relevant (i.e. sublethal) concentrations of contaminants or pollutants, and that this response would persist over time (i.e. beyond the initial, transient increases in transcription and translation rates). Based on prior studies, it was expected by those working on various aspects of the heat shock response that the response was transient in the present of low but constant stressor concentration. S. Lindquist, *Ann. Rev. Biochem.* 55:1151–1191 (1986). Accordingly, one surprising aspect of the present invention is that enhanced concentrations of hsp persist in tissue over time as a result of exposure of an organism to sublethal, environmentally relevant concentrations of pollutants. this aspect of the invention serves as the basis for assays to determine whether an organism has been chronically exposed to one or more pollutants in its environment at sublethal levels.

Another important aspect of the present invention is the recognition of a correlation between elevated levels of heat shock proteins and physiological impairment of an organism at the next level of biological organization (i.e., the whole organism), especially in terms of growth and reproduction of the organism. Such correlation has not been established or even suggested in the prior studies, frequently because the focus was on a molecular and cellular level rather than on the whole organism level. As a result of the present invention, it is now recognized that levels of certain heat shock proteins can be correlated to both stressor (i.e., pollutant) levels and biological impairment of the whole organism. This aspect of the invention serves as the basis for an assay to detect biological damage in an environment due to chronic exposure to a pollutant.

Accordingly, in its broadest aspects, the present invention involves methods for evaluating the integrated stress load on an organism from exposure to environmental contaminants and methods relating hsp concentration to biological damage or impairment of the organism. In the initial steps of these methods, the organism is sampled, and the level of hsp 70, hsp 60, or ubiquitin (singly or in any combination) in a physiological sample of the organism is measured.

The standards utilized in the present invention include a calibration curve that correlates the levels of the chosen hsp with physiological impairment of growth or reproductive processes in the same species as the sampled organism and/or a predetermined baseline level of hsp's (i.e., the hsp level found in organisms in an optimum environment).

Also provided are kits for evaluating general stress in organisms.

With the method and kits of the present invention, it will not be necessary to have an experienced laboratory technician interpret test results. It is also possible to utilize as the measuring method a rapid sandwich immunoassay employing, for example, a dipstick format for the routine and rapid analysis of a large number of samples. The use of monoclonal antibodies can ensure an almost infinite supply of a "standard" reagent for consistent results.

The capacity to perform a large number of analyses quickly and cost effectively using the present invention will allow for more routine and effective environmental monitoring. Because the hsp's are induced in organisms by a wide variety of toxic chemicals, heavy metals, and radiation, the detection of elevated amounts of these proteins is a more universal measure of chronic environmental stress, one that could be used for more general monitoring. For example, positive results could then signal the need for detection and identification of specific contaminants. And just as important, negative results allow one to screen out non-problem environments rapidly with little expense.

Another aspect of the present invention is based on the recognition of the diagnostic potential of the stress peptide response observed in a wide variety of organisms. The expression of these stress peptides may be thought of as a "fingerprint" of complex variations in gene expression that are dependent upon the tissue and the environmental conditions at the time of induction. Once the metabolic details for a particular tissue have been determined, this fingerprinting has the potential to reveal much information about the stress physiology and exposure history of an organism. Fortunately, genes encoding stress peptides and the peptides themselves are remarkably well conserved. Accordingly, a feature of the present invention is the correlation of the amount of stress peptide to standard indices of physiological impairment.

A major advantage of the stress response is that because it is involved in protecting the cell from environmental damage, it provides a direct measure of the cellular physiological state. Thus it has the potential to be more sensitive that existing organismal indices for stress, yet can be correlated to adverse physiological conditions in the organism. Further, as a quantitative response, it would provide the added benefit of evaluating the extent to which an organism is stressed.

The additional advantages of the present invention, particularly in immunoassay embodiments, over the prior art methods, will become clear after considering the detailed description of the invention.

BRIEF DESCRIPTION OF THE DRAWINGS

FIG. 9 is a Western blot of M. edulis mantle tissue against a monoclonal antibody raised against hsp 60 in moth.

DETAILED DESCRIPTION OF THE PREFERRED EMBODIMENTS

Figure 1:
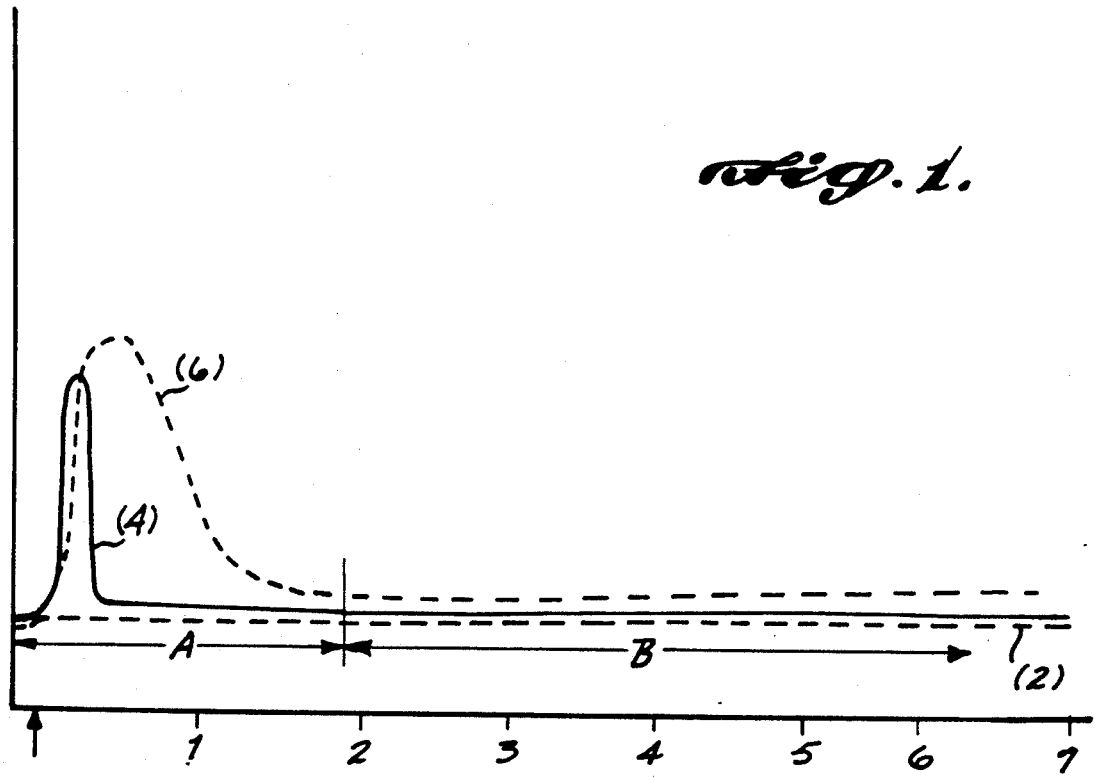
FIG. 1 shows a graphical form, typical data from a metabolic labeling experiment, including levels of synthesis of both an hsp and its corresponding mRNA.

As noted above, the present invention provides assays that are capable of relating levels of heat shock proteins induced by sublethal concentrations of a pollutant to a whole-organism measure of biological damage or physiological impairment, particularly growth or reproductive processes, as well as assays for detecting chronic exposure of an organism to sublethal levels of one or more pollutants.

As used herein, "organism" means any individual biological unit, such as prokaryotes, eukaryotes, algae, and plants. Typically, the organism will be an aquatic organism, such as a marine invertebrate. Particularly preferred organisms are fish (e.g. a fathead minnow), mussels and other molluscs, and sea urchin embryos. Often, individual organisms will be pooled to get a large enough sample size. To minimize false positives, one should avoid sampling species that experience temperature fluctuations in the environment samples (plus or minus 5°-10° C.), or fluctuations in other natural environmental variables that might activate the heat shock protein response. Examples of such natural environmental variables are changes in oxygen concentration (particularly anoxic conditions) and salinity. These constraints can be overcome by monitoring these environmental variables by standard methods, before sampling, to ensure that the sampled organisms are not experiencing fluctuations in such natural environmental variables.

"Environment" refers to the habitat of the organism being sampled.

By "physiological sample" is meant an aggregate of cells, usually, but not necessarily having similar structures and functions such as tissue. In addition to tissue, secretions of the cells might also be used. Preferred examples of such physiological samples are blood, muscle tissue, liver tissue, neural tissue, mucus, amniotic fluid, urine, etc. In some cases, it is preferable to use the whole organism (e.g., when the organism is quite small).

Samples must be collected in such a manner as to not inadvertently activate the heat shock protein response. Proper handling procedures would include ensuring that the sampled organism is not exposed to elevated temperatures after collection and before analysis, ensuring that the sample is not exposed to potential contaminants (e.g., trace metals) or other adverse conditions (e.g., anoxia). The experimental conditions capable of eliciting a heat shock protein response are known tot hose of ordinary skill in the art, and it will be straightforward to ascertain the particular handling conditions that should be used.

By "pollutant" as used herein, is means any substance or condition that is introduced into the environment due to anthropogenic activities and which has demonstrated potential for toxicity. It should be noted that some pollutants (e.g. heavy metals) may also exist naturally in the environment and, at low concentrations, are essential for normal biological function. To the extent that they are necessary for normal biological function, they will typically not elicit a heat shock protein response and generally will not interfere with the assay of the present invention. The EPA has prepared a priority pollutant list which contain some 120+ pollutants which are anthropogenic in nature. These include heavy metals (lead, mercury, copper, etc.), organometallic complexes (tributyltin), pesticides (mirex, DDT), polyaromatic hydrocarbons (PAH's), polychlorinated biphenyls (PCB's) and a number of other chlorinated and unchlorinated hydrocarbons. All of these materials are included within the meaning of pollutant in accordance with the present invention. Thermal pollution is an example of an anthropogenic condition that constitutes a pollutant in accordance with the present invention.

By "biological damage" as used herein is meant any of a range of biological end points or parameters which are indicative of reduced or impaired biological function of an organism. These range from alteration of the function of a critical enzyme, reduced growth rate, tetratogenic effects, reduced reproduction (e.g. egg production, fertilization, metamorphosis, embryo or larval survival), or mortality. Of particular concern are those changes which can affect the ability of the individuals of a population to survive (e.g. growth, reproduction, mortality). It is important that any subcellular parameter such as the heat shock protein response be calibrated against growth, reproduction and related parameters so that the significance of varying degrees of the response can be related to population level effects. This calibration is generally accomplished initially in the laboratory by carrying out exposures to a range of pollutants and monitoring the heat shock protein concentration and other relevant parameters simultaneously (e.g. growth and reproduction). In a preferred example, the heat shock protein response can be correlated to the standard scope for growth assay. In a representative methodology disclosed below in the example section, the heat shock protein response and the scope for growth assay have been measured simultaneously in a representative organism (a mollusc) exposed to a representative pollutant (copper).

An important aspect of the present invention is that it is designed to be used with environmentally relevant levels of a pollutant (or combination of pollutants). By an "environmentally relevant level" of a pollutant is meant a sublethal concentration of the pollutant in the environment with respect to the organism being sampled. A sublethal concentration of pollutant is one which does not result in significantly increased mortality of a population of the organisms over at least one generation and generally a plurality of generations in the population. Such levels of the pollutant are to be contrasted with acute levels of the pollutant, which are considerably higher. Acute levels of the pollutant are those which will result in a significant mortality in a population of the organisms (i.e., about 50%) within a relevant time period, (e.g., on the order of minutes to days). Some exemplary metals and sublethal concentration ranges are shown in the following table:

| Metal | Exemplary Sublethal Range ($\mu g/l$) |
|---|---|
| Al | $\leq 1,900$ |
| As | $\leq 720$ |
| Cd | $\leq 210$ |
| Cr-III | $\leq 19,000$ |
| Cr-IV | $\leq 32$ |
| Cu | $\leq 250$ |
| Pb | $\leq 5,500$ |
| Hg | $\leq 5$ |
| Ni | $\leq 9,000$ |
| Se | $\leq 270$ |
| Ag | $\leq 150$ |
| U | $\leq 48,000$ |
| Zn | $\leq 2,300$ |

It is also important to note that the present assays are designed to determine levels of one or a combination of heat shock proteins induced in an organism in a long-term (i.e., chronic) exposure situation to sublethal concentrations of a pollutant or pollutants. Thus, the assay will provide especially useful information when it is performed in a time period following an initial transient hsp response due to exposure of the organism to the pollutant or stressor. The initial, transient hsp response is that time period following initial introduction to the stressor in which levels of transcription and translation of heat shock proteins are substantially elevated above baseline levels. See FIGS. 1 and 2. In FIG. 1, the rate of hsp synthesis is plotted against time in days. The point at which a pollutant or stressor is added is marked by a vertical arrow on the time line. The baseline hsp synthesis rate is shown by the horizontal broken line (2); the rate of hsp messenger RNA synthesis is shown by the solid line (4); and the rate of hsp synthesis is shown by the dotted line that peaks at <one day (6). The transient hsp response period, A, is indicated as is the long-term or chronic period B. In this graph, the rate of hsp synthesis drops to about 2 times the baseline rate during the chronic period.

Figure 2:
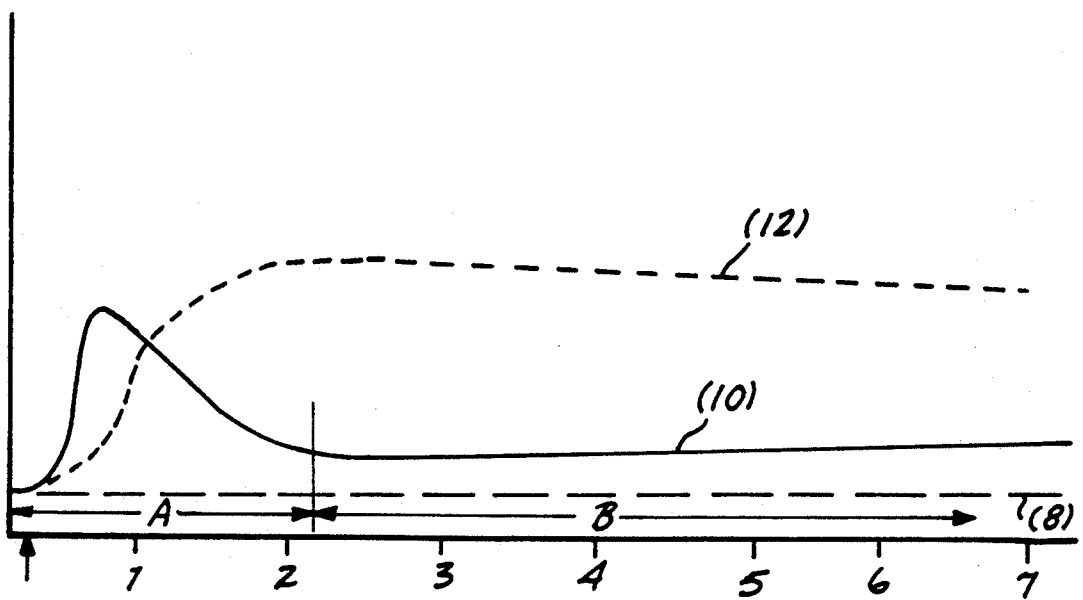
FIG. 2 shows in graphical form typical data obtained by measuring the concentration of an hsp and its corresponding mRNA as a function of time.

In FIG. 2, the concentration of hsp or messenger RNA in a physiological sample is plotted against time in days. The point at which a pollutant or stressor is added is marked by a vertical arrow. The baseline is shown by the horizontal broken line (8); the concentration of hsp messenger RNA is shown by solid line (10); and the concentration of hsp is shown by broken line (12). The transient hsp response period, A, is indicated as is the long-term chronic period, B. In this graph, the concentration of mRNA drops to about 10 times the baseline rate during the chronic period.

Substantial elevations of hsp's are those that can be detected by fluorography of an SDS gel following metabolic labelling. See FIG. 7. As metabolic studies have indicated, these levels are expected to revert to control levels within a relatively short period of time (i.e. about 12 hrs.) in the species of organism being sampled.

To determine whether an environment is in the long-term, chronic exposure time period and sublethal concentration range of pollutant, two assays are conducted, each being conducted identically but at two separate times. This can be readily accomplished by sampling an organism and measuring a level of a heat shock protein in this organism and subsequently, after passage of a period of time, measuring the concentration of the same heat shock protein in another organism of the same species as the first. The time period between the two samplings should be long enough so that if the organism is in the transient response period (a phase in which the level of hsp is increasing at an exponential rate, i.e., a log phase of hsp increase), a significant difference in the concentration of an hsp can be detected between the two measured concentrations of hsp. Performing assays at about the same time on different days is preferred in part because samplings taken at different times of the day may result in more variability between measurements due to differences in temperature or other conditions that can affect the hs response. Since the chronic exposure time period will generally result in a relatively constant level of heat shock protein, a comparison will be made between these two measurements and if the level of the heat shock protein being measured remains relatively constant (i.e. $\pm$about 50%, preferably $\pm$about 35%, most preferably $\pm$about 25% of the first measurement), then it can be concluded that the organism is in the chronic exposure time period. Chronic exposure levels of hsp will be substantially higher than control or baseline levels of hsp (e.g., at least 2 times the baseline levels; more commonly, at least 4 times and occasionally up to about 10 times or more of the baseline level). It should be noted that acute transient responses interfere with the purposes of the present assay and would not be correlated with changes in growth and reproduction.

A determination of whether the organisms being sampled are being exposed to acute rather than sublethal levels of stressors and are in the long-term rather than a transient hs response period can also be done on the basis of either direct observation, other organismal indices, or other environmental assays. For example, acute levels of some stressors will result in death of a variety of organisms in the vicinity of the organism, including some of the species which is being sampled, which can be directly observed by the sampler. The sampler may be aware of high levels of stressor in the environment based on knowledge of recent events, such as recent accidental release of high concentrations of a stressor in the vicinity of interest. If the organism is experiencing an exposure to acute levels of a pollutant or is in the transient hsp response period to a pollutant, then the assay of the present invention will not be especially advantageous for use. The sampler may also desire to carry out analysis of water, air, etc. in the habitat to detect the presence of acute levels of pollutants.

After obtaining a physiological sample of the organism being sampled, it is generally necessary to solubilize the heat shock proteins in the sample. This can be accomplished by any method known in the art, generally involving cell disruption. Cell disruption may be accomplished by homogenizing or sonicating the samples, in preferred embodiments.

The particular heat shock proteins that are measured in accordance with the present invention, in the organism of interest, are those designated as hsp 70, hsp 60, and ubiquitin. It should be noted that these designations do not refer to a single protein, but rather to a family of iso-proteins. The hsp 60 and hsp 70 families have, on average, the molecular weight (in kilodaltons) designated by the number (60 or 70) in the name. Generally, the molecular weight, as determined by SDS-PAGE, will have as its mid-point the indicated number, and will range plus or minus five kilodaltons. Thus, hsp 70 refers to a family of iso-proteins having molecular weights of from about 65 to about 75 kilodaltons. Hsp 60 refers to a family of iso-proteins having molecular weights ranging from about 55 to about 65 kilodaltons. These heat shock proteins are described in greater detail hereinbelow.

There are two major members of the most highly conserved stress protein, the hsp 70 family, each of which is present in multiple isoforms (Lindquist, S., *Ann. Rev. Biochem.* 55:1151-1191 (1986). The larger protein of the two 73 kDa in mammals, is often referred to as the hsp cognate because it is found in unstressed cells and also exhibits a marked increase in synthesis upon exposure to various stressors. The smaller protein, 72 kDa, is only synthesized upon exposure to stress and is not found in the cell under normal conditions. Although these two hsp's are closely related and have similar biochemical properties, they are distinct gene products.

As for the functional aspects of these important proteins, a general picture is now emerging in which hsp 70 acts to either stabilize or solubilize a target protein. Under normal conditions such binding may serve a "chaperone" function for newly synthesized secretory and organellular proteins by helping them to translocate across a membrane (Chirico, W. J., M. G. Waters, G. Blobel, *Nature* 333:805-810 (1988), Deshaies, R. J., B. D. Koch, M. Weiner-Washiburne, E. Craig, R. Schekman, *Nature* 332:800-805 (1988)). Another member of the hsp 70 family, called BiP or grp78, is also found under normal conditions and has recently been shown to be transported into the endoplasmic reticulum where it may perform a similar chaperone function for proteins transported into this compartment (Craig, E. A., J. Kramer, J. Kosic-Smithers, *Proc. Natl. Acad. Sci. U.S.A.* 84:4146-4160 (1987)).

The highly inducible hsp 72 in conjunction with the other hsp 70 proteins may perform a similar role in cells experiencing stress. A major feature of stressed cells is the loss of integrity of the nucleolus and the associated inhibition of rRNA synthesis and ribosomal assembly. Under stress, hsp 72 rapidly migrates to the nucleolus where it is speculated to resolubilize denatured pre-ribosomal complexes and help restore nucleolar function during recovery from stress. During recovery it migrates to the cytoplasm and associates with ribosomes and polyribosomes (Welch, W. J., J. R. Feramixco, *J. Biol. Chem.* 259:4501-4510 (1984) where it is speculated that it may bind to denatured proteins and in an ATP dependent manner facilitate their resolubilization (Pelham, H. R. B., *Nature* 332:776-777 (1988)).

The hsp 60 family, found in the mitochondria, is believed to be another "chaperoning" protein which facilitates the translocation and assembly of oligomeric proteins into that compartment (Cheng, M. Y., F-U Hargl, J. Martin, R. A. Pollack, F. Kalousek, W. Neupert, E. M. Hallberg, R. L. Hallberg, A. L. Norwich, *Nature* 337:620-624 (1989). It is homologous to the bacterial hsp GroEL and the Rubisco-binding protein of chloroplasts (Reading, D. S., R. L. Hallberg, A. M. Myers, *Nature* 337:665-659 (1989), forms large aggregates in the matrix of the mitochondria, and is essential for the assembly of oligomeric complexes imported into the mitochondria.

Ubiquitin is a small molecular weight (7 KDa−1 KDa) protein found in all eukaryotic cells. Under normal conditions it is involved in the non-lysosomal degradation of intracellular proteins (Schlesinger, M. J., *Atlas of Sci. Biochem.* 161-164 (1988). When ubiquitin is conjugated to proteins by a ubiquitin-protein ligase system these proteins are selectively degraded. Ubiquitin synthesis increases with exposure to heat and is an essential component of the cellular stress response (Finley, D., E. Ozkaynak, A. Varshavsky, *Cell* 48:1035-1046 (1987).

Hsp 70, hsp 60, and ubiquitin (alone or in continuation) are measured for the purposes of the present assays rather than other known hsp's, since these latter hsp's are either not as widely conserved from species to species of they are induced by other factors (e.g., hormones) that can interfere with the overall goal of the assays: to correlate hsp concentration with biological damage to the organism's habitat.

Measuring the concentration of the heat shock protein in the organism may be accomplished by any technique known for measuring concentrations of proteins, but preferably will involve an immunologic binding partner of an hsp. For example, the level of hsp 60, hsp 70 or ubiquitin can be measured by using a monoclonal or polyclonal antibody capable of specifically binding with one or a combination of these heat shock proteins. An example of a particularly preferred polyclonal antibody is one described by Miller et al. in *Insect Biochemistry*, 17:417-432 (1987). The immunological method may be carried out in a variety of standard forms, including an ELISA, RIA, sandwich assay, Western blot, dip stick method, etc. Additional details on these methods, as applied to the present invention are provided in the examples section below. Non-immunological methods of quantitating these proteins can also be used. The particular method of measuring the concentration (quantitatively or semi-quantitatively) of the heat shock proteins is not critical, as long as the concentration of the protein or the total amount of the protein in the organism, tissue, or secretion can be determined.

The measured concentration value of the hsp may preferably be expressed in terms of the biomass used in the measurement step. Accordingly, it may be desirable to monitor the concentration of an invariant protein simultaneous with the hsp concentration measurement as a control.

The correlation or comparison step or the present invention includes developing a set of appropriate "calibration curves" that correlate the results of the stress peptide assay with the onset of physiological stress in a selected organism. These calibration curves are developed through a series of detailed laboratory studies in which organisms are exposed to progressively increasing doses of given stressors. Physiological stress is evaluated by monitoring growth rates and reproductive success. Growth rates are measured directly (e.g., increased weight, length, etc.) and indirectly (e.g., scope for growth). Reproductive success is evaluated by monitoring gamete production and fertilization success. To facilitate standardization and increase the utility of the calibration curves, these calibration studies are designed so that the data can be compared directly with current EPA data sets.

The calibration studies can be carried out in parallel with both laboratory-exposed organisms and field-exposed organisms. Subsamples from these studies can be assayed for the hs response (hsr) and other subsamples can be assayed for toxicity. Using standard EPA approved methods to evaluate lethality and growth and reproductive impairment. This can result in the cross-calibration of the heat shock assay with EPA methods under both controlled laboratory conditions and actual field conditions. Several different classes of stressors are used to develop these calibration curves including physical stressors (e.g., heat) and the major chemical stressors (e.g., metals and xenobiotic organic compounds). Calibration curves are developed for several groups of organisms including invertebrates (mussels), vertebrates (fish) and aquatic plants (e.g., phytoplankton).

By baseline heat shock protein concentration level is means a concentration of the heat shock protein in an organism in an optimum environment; that is, an environment free of pollutants that cause a heat shock response. The baseline level will typically be less than about 10% of hsp concentration of exposed organisms and will often be about zero for inducible hsp's. For constitutive hsp's the level will be greater than zero but still significantly less than the hsp concentration induced by pollutants. Baseline concentrations can readily be determined by preliminary hsp concentration measurements in an organism.

Methods of generating calibration curves are presented in the examples section below.

The embodiment of the method in an assay kit format makes its practice more convenient and commercially marketable. Accordingly, numerous assay kit formats can be developed to practice the method of the present invention. A kit for practicing the most preferred embodiment of the present invention, a sandwich immunoassay, would include a first antibody capable of combining with an hsp by the organism exposed to the stressor. In order to measure or assay the hsp, the antibody should be capable of being detected, e.g., radio or enzymatically labeled. Additional immunoassay formats include competitive assays and disassociation assays. A competitive assay kit would include an antibody capable of binding with the hsp synthesized by the organism, wherein the antibody is associated with a substantially insoluble support. The kit would also provide a known amount of labeled hsp standard to compete with the stress-related substance in the organism. A disassociation assay kit also includes an antibody associated with a substantially insoluble support and a known amount of labeled hsp. Also included in the kit would be an appropriate standard.

The invention now being generally described, the same will be better understood by reference to certain specific examples, which are not intended to be limiting of the present invention, unless so indicated.

EXAMPLES

The Antibody Probe Technology

The consequence of large increases in the transcription of mRNA from certain genes after environmental perturbation is the synthesis and accumulation of stress peptide in the cell.

The accumulation of hsp's in cells can be used to evaluate the stress load in organisms that have been exposed to environmental contaminants and, further, to determine the extent of the stress through quantitation of the hsp relative to identical unstressed organisms. The amounts of major individual stress peptides can be determined quickly and accurately even in the presence of other cellular peptides by measuring the binding of antibodies specific for the heat shock peptides (antigen).

The development of antibodies for use in the present invention is based on the typical immune response of organisms to antigens. When an animal is confronted by an antigenic (e.g., hsp) stimulus, it responds by producing a large variety of antibody structures (polyclonal antibodies) that interact specifically with that antigen. The antigen:antibody interaction can be visualized in much the same manner as the lock and key analogy used for substrate:enzyme interactions.

Recently, a hybrid melanoma (hybridoma) technique has been developed in which each antibody-producing cell makes just one antibody structure, a monoclonal antibody, directed at a single antigenic determinant. The monoclonal antibodies useful in the present invention are obtained by the process discussed in Milstein and Kohler and reported in *Nature*, 256:495-497 (1975). Details of this process are well known and will not be repeated here. One advantage of hybridoma antibodies over conventional polyclonal antibodies is the possibility of a permanent supply and chemical reproducibility. Once a reagent is considered optimum, all observations, including cross-reactivity patterns, stability during storage, and other manipulations, will be valid for new batches prepared in the same way. These are important characteristics for a reagent that is to be marketed as part of a commercial kit. Thus, in a preferred embodiment of the present invention, monoclonal antibodies will be prepared against the major heat shock peptides, and those antibodies that differentiate the major hsp's from the "cognate" or "constitutive" peptides will be employed as in the ligand-receptor of the present invention. However, polyclonal antibodies may also be employed in the method of the present invention.

Either monoclonal or polyclonal antibodies may be employed as part of a sandwich or competitive enzyme-linked immunosorbent assay (ELISA). In this procedure, the purified antibody is labeled by attaching an enzyme that can react with a colorless substrate to give a colored product. The amount of colored product released in a fixed period of time depends on the concentration of enzyme, and this is also a measure of the amount of antibody present. The antibody in turn will bind in proportion to the amount of stress peptide (antigen) that is present. The amount of colored product produced in the reaction is therefore a measure of the amount of heat shock protein present. The intensity of the colored product can be quickly and conveniently compared with the color of other standard solutions containing unstressed cell extracts and varying amounts of hsp's.

In a representative sandwich ELISA, purified anti-hsp 70 antibody is placed in the wells of microtiter plates in order to immobilize it to the plastic surface; i.e., solid carrier. Cells or small amounts of tissue containing the hsp will be disrupted and placed in the wells of the microtiter plates to allow the antigen to attach to the immobilized antibody. The cell/tissue extract is removed, the wells are washed, and a second antibody that is labeled with enzyme is placed in the well. The excess antibody remaining unbound to the immobilized antigen is then removed and the color-producing reaction is initiated by the addition of the enzyme substrate.

For the purposes of an immunoassay, monoclonal antibodies are produced that are specific for hsp 70, hsp 60 or ubiquitin. Hsp 70 shows a marked degree of conservation in its structure amongst widely diverse organisms, and antibody against hsp 70 from one species will interact with hsp 70 stress peptides from other species. Thus, the monoclonal antibodies can ultimately be used to assay for environmental stress among a number of different terrestrial and aquatic organisms.

There are a number of different modifications of the ELISA system that can be used to develop the antibody as part of a kit. Those that are part of the present invention include: (1) competitive inhibition or disassociation procedures for use with purified stress peptide; (2) the use of polyclonal antibody in the first stage of the sandwich assay followed by the use of enzyme-linked monoclonal antibody; (3) the simultaneous use of several different monoclonal antibodies to increase the sensitivity of the assay; and, (4) modification of the assay for use as a "dipstick" indicator in the field.

The labeled monoclonal antibodies used in the present invention may be provided with the same labels used in prior art immunoassays. Among these being mentioned, fluorogenic labels for detection by fluorimetry as described in U.S. Pat. No. 3, 940,475 and enzymatic markers as described in U.S. Pat. No. 3,645,090. Also, the antibodies may be labeled with radioisotope such as I-125 using, for example, the procedure of Hunter and Greenwood, *Nature*, 144:945 (1962) or that of David et al., *Biochemistry*, 13:1014–1021 (1974).

Peptide or Protein Purification

The organism maintained under optimal growth conditions will be stressed by the inclusion in the medium of $CuCl_2$ (final concentration pCu=9) or by heating the medium. Twenty-four hours later, the cells will be harvested using standard procedures. The hsp's will be identified and their purification monitored by using "Western blotting" in a procedure involving the identification of the immobilized peptides by polyclonal antibodies elicited against synthetic peptides corresponding to conserved regions of the major stress peptides or anti-SP prepared against peptides isolated from different organisms.

The following is an exemplary process for purifying hsp 70 peptides or proteins. The principal hsp's can be isolated from the disrupted cells by a combination of column chromatography (DEAE-cellulose, Sepharose 6B-CL, Sephacryl S-300, hydroxylapatite) and high performance liquid chromatography. The known affinity of the hsp's for ATP will allow for the use of ATP-Sepharose in their purification. Homogeneity of the peptides will be assessed by sodium dodecyl sulphate-polyacryl-amide gel electrophoresis (SDS-PAGE) and N-terminal amino acid analyses. See, Welch and Feramisco, *J. Biol. Chem.*, 257:14949–14959). To confirm that the purified peptides are those specifically induced by environmental stressors, comparative two-dimensional PAGE will be performed with purified peptide and unstressed and stressed cell extracts.

Peptide Amino Acid Sequence Data

Each of the major stress peptides (hsp 70, hsp 60) could be subjected to partial sequence analysis (about 30 residues) from the N-terminus using a microsequencing instrument. With this data, it will be possible to define corresponding nucleotide sequences based on genetic code assignments. This information, together with published nucleotide sequence data of conserved regions of the genes from other organisms, will allow one to determine the appropriate nucleotide sequence(s) to employ for synthesis of gene probes.

The amino acid sequence data will also confirm that the N-terminus of hsp 70 from this organism is homologous to that of hsp 70 from numerous other species. This will allow one to use the synthetic peptide, VGIDLGTTYSC, polyvaline-clycine-isoleucine-aspartic acid-leucine-glycine-threonine-threonine-tyrosine-serine-cysteine, as an antigen in the production of an antibody that could be used as a probe to measure hsp 70 levels in this and many other organisms as well. This sequence is representative of stress peptide sequences from several different sources. See, for example, Chappell et al., *Cell* 45:3–123 (1986). This antibody may also be used in the "Western blot" procedure to identify stress peptides.

Production and Purification of Antibodies

Protocols for the establishment and maintenance of monoclonal antibody-producing hydridomas are now well established and are employed here. See, Kipps and Herzenberg, *Handbook of Experimental Immunology*, 4th Ed. Blackwell Scientific Publications, Oxford (1985). Essentially, the technique involves polyethylene glycol-induced fusion of two cell types: mouse myeloma tumor cells and antibody-producing B cells from mice that have been immunized against stress peptide. The mouse myeloma cell lines (for example, Sp2/0-Ag14 or P3X63-Ag8.653) are obtained from exponentially growing cultures prior to cell fusion. Equal members of $\beta$-lymphocytes prepared from spleens of immunized mice are incubated with myeloma cells for fusion. The fused cells retain the immortality of the myeloma cell line but continue to secrete the antibody of the B cell. To select cells that have undergone fusion, culture conditions will be chosen such that the fused coils, but neither of the two parental cells, will survive. The cells will then grow in a large number of wells in a tissue-culture plate, screened (by ELISA) to determine if they produce the desired antibody, and then "cloned" to ensure that the cell line produces homogeneous antibody of high affinity. These fused cells will be maintained indefinitely in tissue culture, assuring a constant supply of antibody with invariant properties for quantitative immunological assay.

Polyclonal antibody may be used in "Western blot" identification of peptides and possibly as well as part of the sandwich ELISA. For its preparation, purified peptide (or chemically synthesized peptides linked to a heterologous carrier peptide) mixed with Freund complete adjuvant will be injected into standard laboratory rabbits. Two weeks after the initial injection, additional peptide in complete Freund adjuvant will be injected. Serum will be prepared ten days after this boost. The antibody so produced will be partially purified by ammonium sulphate precipitation (40%) of the sera and then purified by affinity chromatography on columns of stress peptide covalently coupled to Sepharose 4B.

Purified antibodies may be "labeled" with the enzyme alkaline phosphatase. When associated with its specific stress peptide (antigen) and in the presence of the substrate p-nitrophenol phosphate, alkaline phosphatase linked to the antibody will produce a yellow color (p-nitrophenol), which can be visually or spectrophotometrically measured.

Detection of Elevated Levels of Hsp's and RNA's of Hsp's

Whole cells or tissue fragments of an organism are disrupted and solubilized in guanidine hydrochloride. The mRNA is selectively precipitated with ethanol and placed on a supporting medium as a "dot." Specific mRNAs are detected by standard dot-blot hybridization using the labeled genetic probe. The amount of hsp mRNA is calibrated with the use of standards.

For detection of elevated levels of hsp in cells, the cells are disrupted to ensure the complete release of hsp's from the nucleus using a combination of simple mechanical and nondenaturing detergent solutions and then incubated in the wells of microtiter plates containing immobilized antibody. The enzyme linked to the antibody will produce a color reactant whose concentration will be proportional to the amount of a particular stress peptide.

Several different cell disruption techniques may be used depending on effectiveness for each different organism. Disruptive techniques that are employed include: (1) mechanical disruption using a Teflon-coated Dounce homogenizer or similar apparatus; and, (2) ultrasonic disruption or disruption with a blender or similar apparatus. Additional lytic techniques employed include: (1)lysis in NP-40 (0.5% solution) in 10 mM Tris-Cl (pH 8.0), 0.15M NaCl, and 0.02% NaN$_3$; and, (2) hypotonic lysis in sucrose. Cells or tissues are suspended in 10 ml of 0.32M sucrose (pH 7.4) and disrupted in an homogenizer. Protease inhibitors will be included in all buffers used for cell or tissue disruption.

Many different factors influence the overall induction time and extend of response in terms of mRNA and hsp synthesis following stress. These include the severity of the stress, duration of stress, whether the environmental stress developed quickly or over along period of time, whether there has been a recovery period, and the duration of this recovery. Thus, in the environment there may be times when the stress response may induce RNA synthesis but conditions are such that peptide synthesis may not be able to occur. In such a case, the gene probe embodiment of the present invention will prove useful. In the chronic exposure assay of the present invention, one generally finds that RNA synthesis approaches (normal) unstressed levels, but stress peptide accumulation is at a level that can be detected with an antibody-based immunoassay.

In some stress conditions (e.g., anoxia), induction of hsp's does not occur until there is a "recovery" period. Under certain conditions, therefore, it may be appropriate to remove the organism(s) to a controlled environment and then determine if the organism(s) was stressed by assaying for the initiation of hsp RNA or hsp through the use of the DNA or antibody probes.

HSR

Although the regulation of gene expression in the hs response is well understood, very little is known about if and how stress peptides function in cellular metabolism to enhance tolerance. Applicants have tested the hypothesis that the tissues of two molluscs, the mussel *Mytilus edulis* and the limpet *Collisella pelta*, respond to stressful conditions by synthesizing hsp's. In order to determine if they elicit the hs upon exposure to heat shock, organisms were transferred from 40° to 31° C. for two hours. Appropriate tissues were then dissected and incubated in vitro with 35-S methionine for two hours. Samples were homogenized, centrifuged, and individual peptides were separated by SDS-PAGE electrophoresis. The incorporation of radiolabeled amino acids into each peptide band was determined by autoradiography.

Both species exhibited the hsr in response to heat shock in all tissues examined. Differential patterns of peptide synthesis occurred in the gill tissues of heat-shocked mussels relative to controls. In heat-shocked gills at least nine new peptide bands with molecular weights of 80, 70, 68, 61, 47, 43, 42, 32, and 29 kDa incorporated significant 35-S relative to controls. Also, relatively less label was incorporated into other cellular peptide bands that were heavily labeled in the controls. Similar stress peptide responses were observed in the foot and viscera of limpets.

Induction of stress peptide synthesis was also observed in both species upon exposure to Cd. In these experiments, mussels and limpets were exposed to free Cd ion activities of $10^{-9}$ and $10^{-7}$M using a Cd-EDTA chelate buffer. Within 72 hours, an increased synthesis of stress peptides was apparent in both species. However, unlike the response elicited by heat shock, the repression of "normal" cellular peptides was observed to a lesser degree when elicited by Cd. The present inventors have carried out preliminary experiments that indicate that the hsr is expressed in organisms exposed to stressors in situ.

Figure 3:
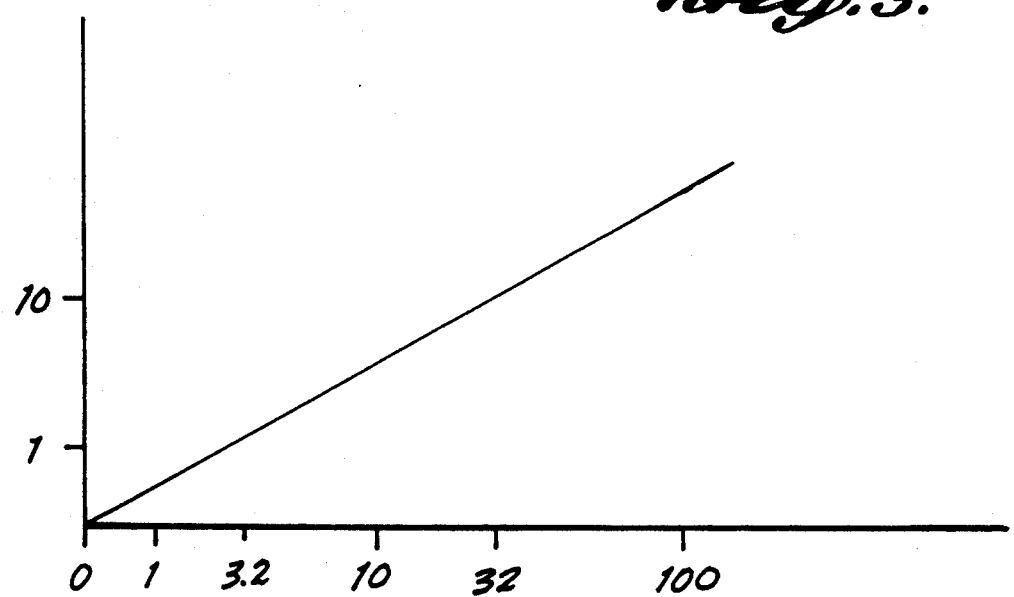
FIG. 3 shows a plot of the $-\log_{10}$ or hsp 70 concentrations versus $-\log_{10}$ of stressor concentration. This particular data was obtained in a mollusc (*Mytilus edulis*) exposed to varying Cu concentrations for seven days.
Figure 4:
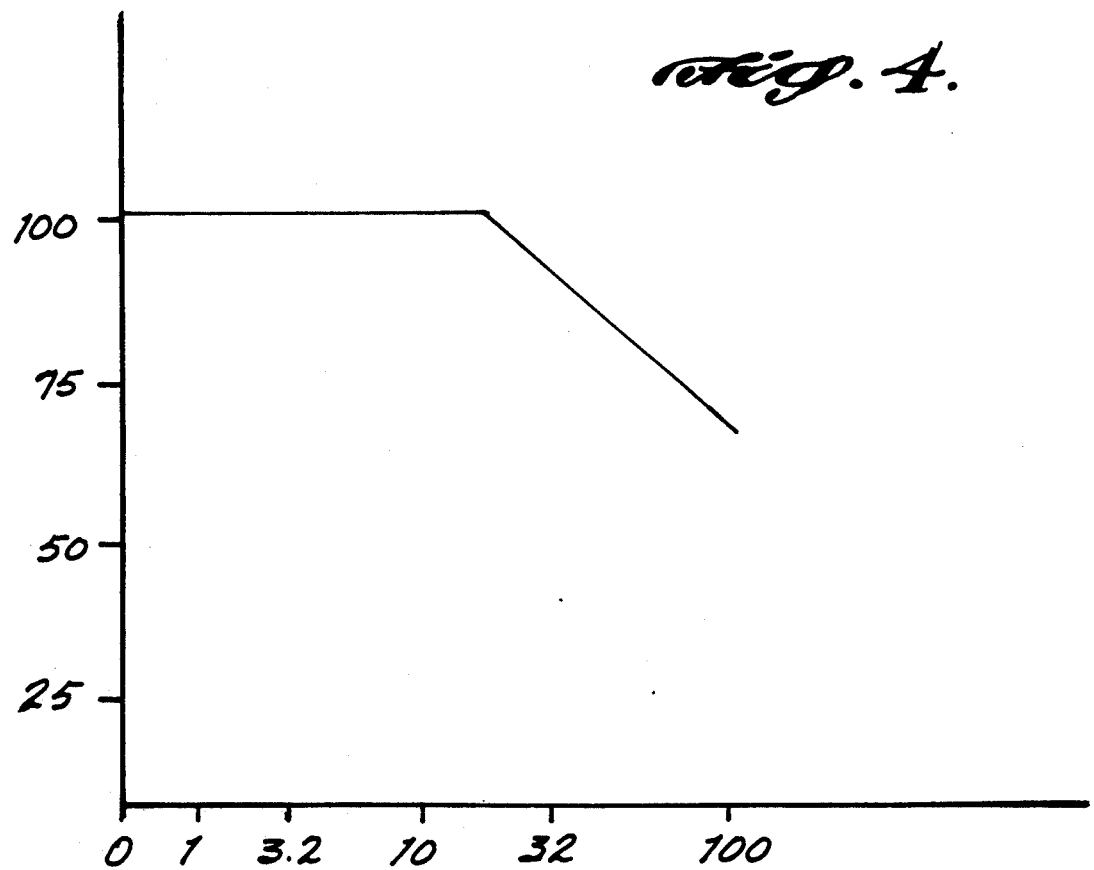
FIG. 4 is a plot of an organismal indicator of stress (scope for growth) versus $-\log_{10}$ stressor concentration (Cu).

In another experiment, Mytilus was exposed to 32 ppb Cu and sampled over time for one week. Dot blots with the polyclonal against hsp 60 show increased hsp 60 accumulation with time. Mytilus was exposed to a range of Cu concentrations (0, 1, 3.2, 10, 32, 100 ppb) and tissue samples were collected after one week for metabolic stress index which is basically an abbreviated energy budget. Inhibition of scope for growth (SFG Y-axis) was observed at 32 and 100 ppb (X-axis) as shown in FIG. 4. No dramatic differences were seen in translational patterns from the metabolically labeled tissue. The inventors used dot blots to semi-quantify hsp 60 with the moth polyclonal described by Miller et al. The inventors found significant increases in hsp 60 concentrations in tissues from organisms exposed to 3.2 ppb Cu and above. Further, there was a linear relationship between the log of the Cu concentrations (X-axis) and the log of hsp 60 concentration (Y-axis) as shown in FIG. 3. These data are both significant and promising because they demonstrate that Mytilus does exhibit a sustained accumulation of hsp 60 at environmentally relevant Cu concentrations. Further, a response could be detected at a Cu concentration an order of magnitude lower than an organismal stress indicator currently believed to be one of the most sensitive (SFG).

Figure 5:
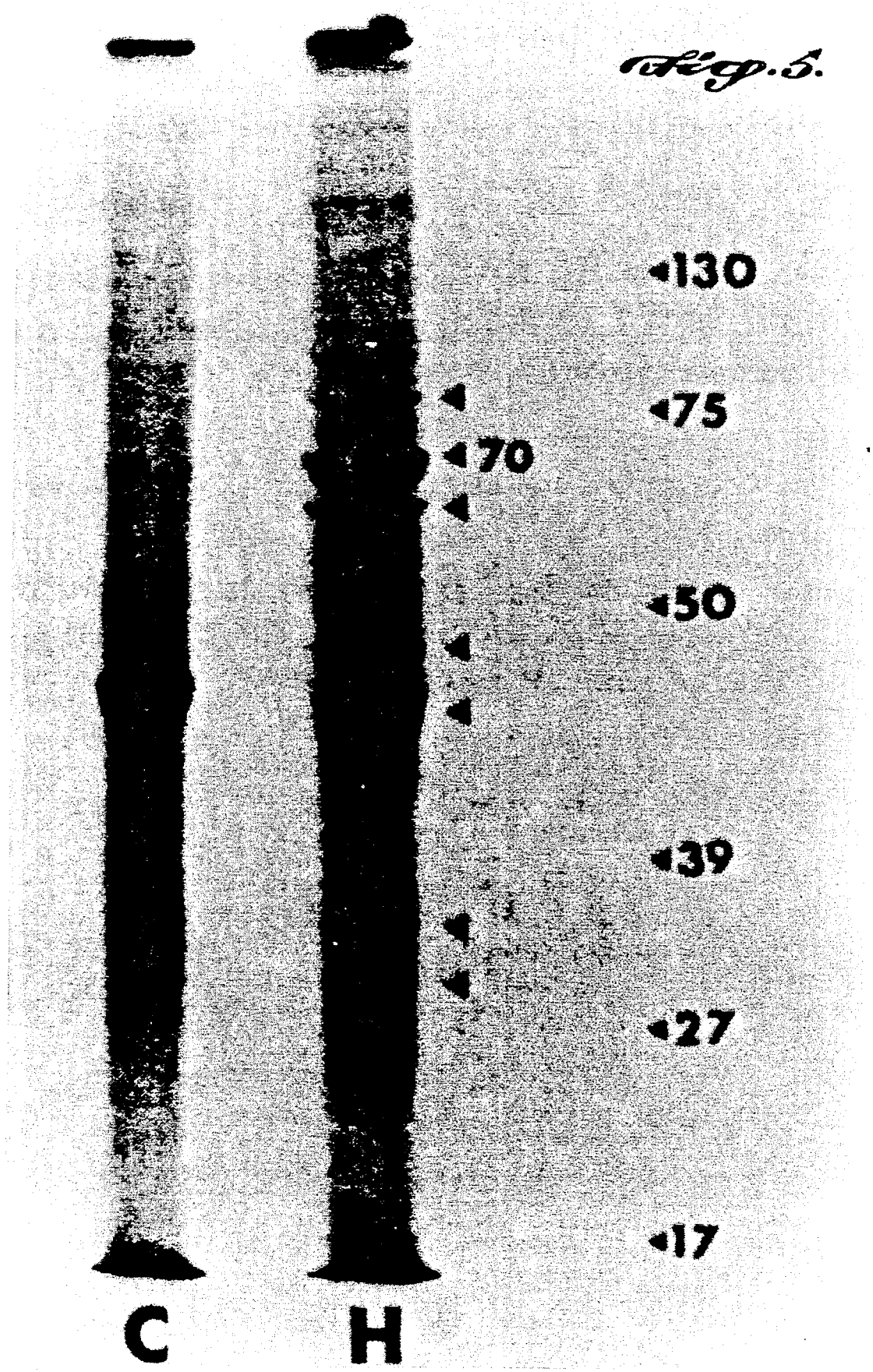
FIG. 5 shows the heat shock response in gill tissue of *Mytilus edulis*.

FIG. 5 shows the heat shock response in gill tissue of Mytilus edulis. The control (C) was maintained at 17° C., while the heat shock (H) sample was exposed in vivo to a heat shock for one hour at 31° C. Tissues were then incubated in 35-S methionine, homogenized and equal protein was loaded for one dimensional electrophoresis (SDS-PAGE). The gels were subsequently fluorographed. Arrows at the far right indicate molecular weight markers of 130, 75, 50, 27 and 17 kDa, respectively. Arrows next to the heat shocked sample indicate stress proteins of 80, 74, 72, 60, 47, 32 and 29 kDa, respectively. The arrow next to the doublet at 43 kDa is believed to be a common breakdown product of hsp 70.

Figure 6:
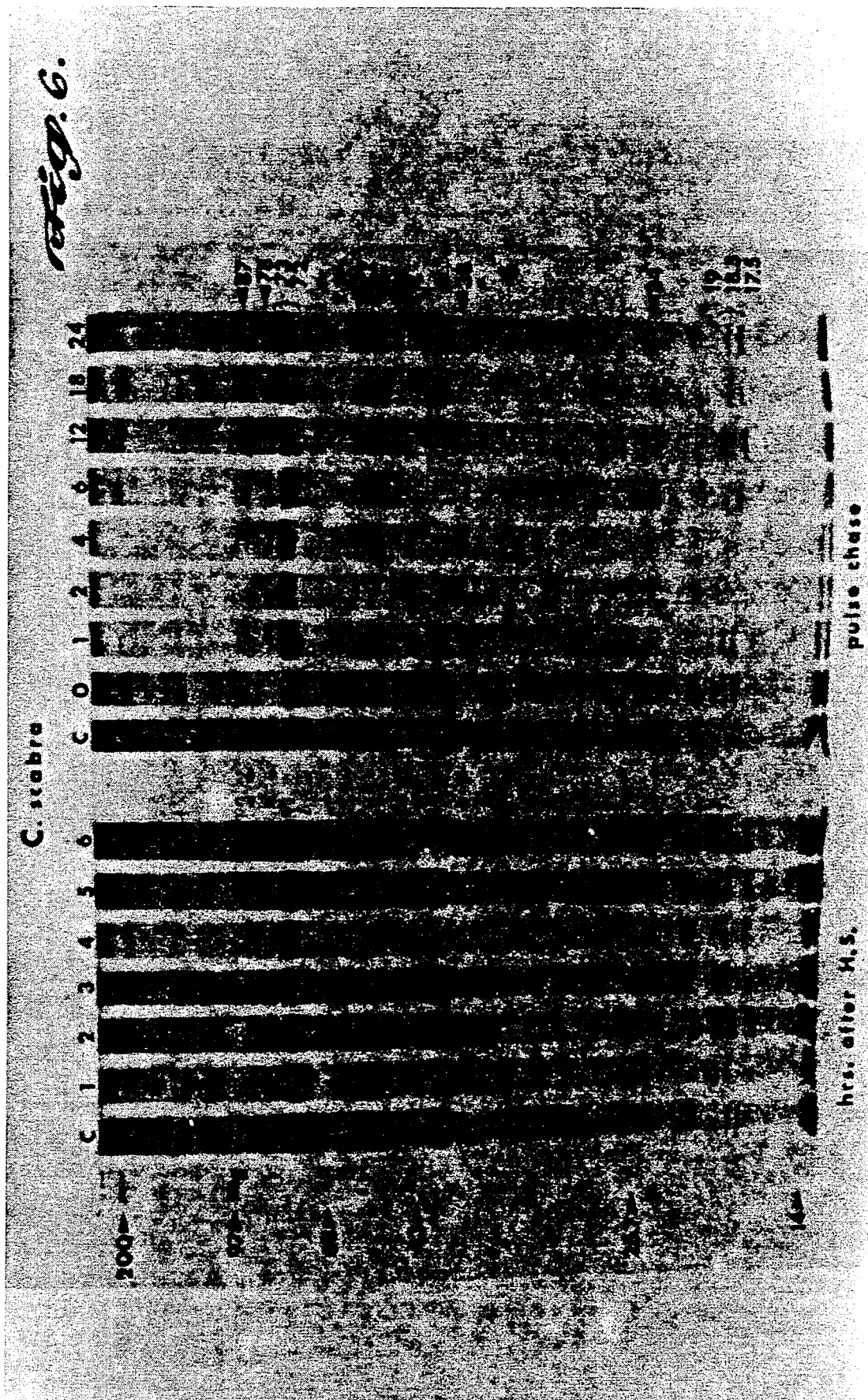
FIG. 6 is a fluorograph of Collisella mantle tissue from induction and half life experiments.

FIG. 6 is a fluorograph of Collisella mantle tissue from induction and half life experiments. Samples were processed as described in FIG. 5. Arrows at the right of the fluorograph identify hsp's of 87, 78, 73, 38, 24, 19, 18.5 and 17.5 kDa, respectively. Molecular weight markers are shown on the left.

Left: Incorporation of $^{35}$S-methionine into proteins in C. scabra mantle tissue at different points in time after a 1 hour, 31° C. heat shock. Limpets were heat shocked in vivo and incubated for one hour at the times indicated to examine how long the response was induced after heat shock. The control (C) was not heat shocked. Increased synthesis of hsp's can be seen for at least 6 hours after heat shock.

Right: Incorporation of $^{35}$-S-methionine into proteins in C. scabra mantle tissue during a pulse chase experiment to examine the half life of the hs proteins. Limpets were heat shocked for 31° C. for 1 hour, immediately pulsed with 35S methionine for one hour, and incubated in cold methionine over time. The numbers above the sample represent the hours that the tissue was incubated in cold methionine after heat shock. The control (C) was not heat shocked. Hs proteins remain prominent 24 hours after heat shock.

Figure 7:
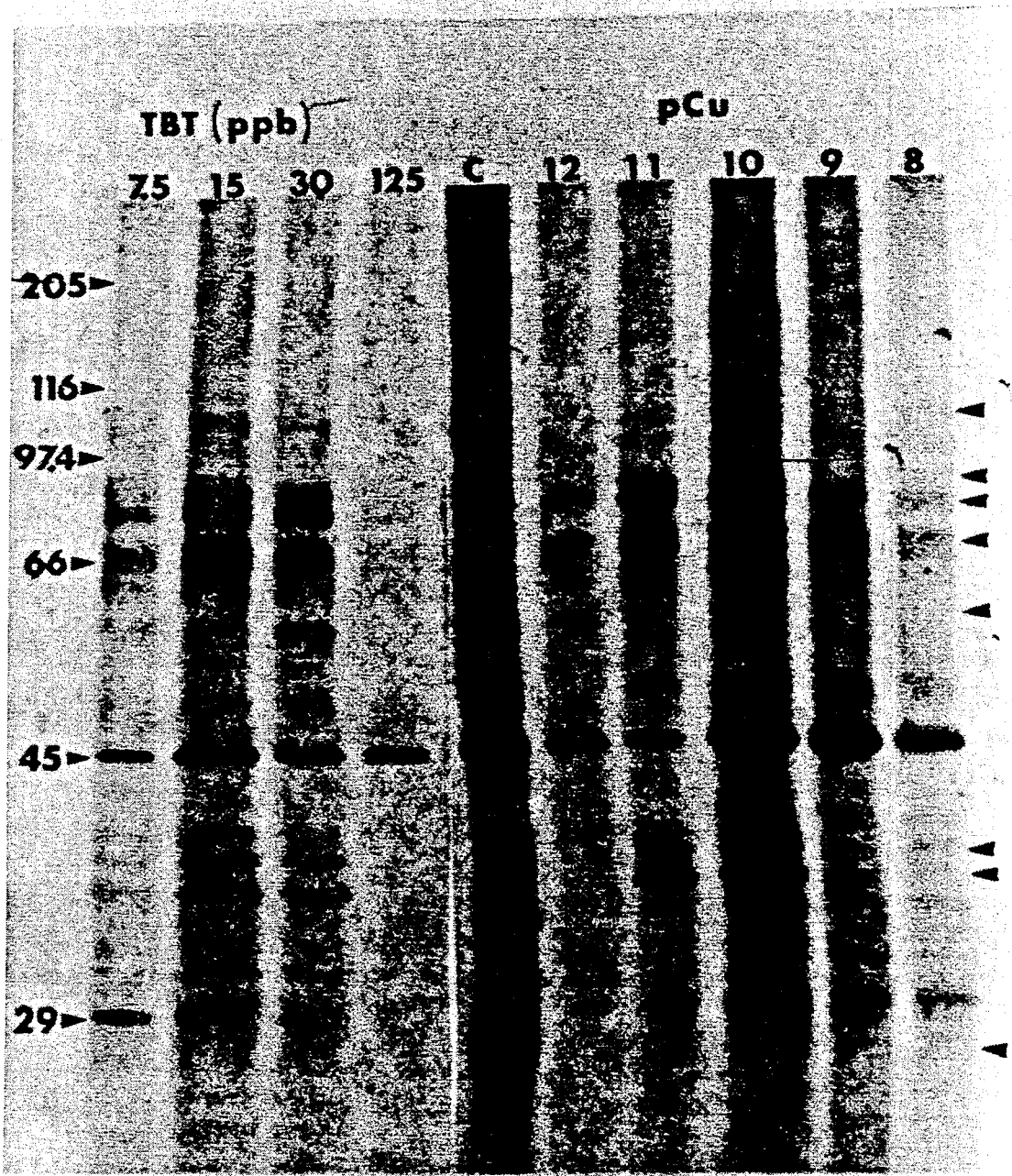
FIG. 7 shows induction of the heat shock response in hemolymph of *M. edulis* exposed to tributyltin and copper.

FIG. 7 shows induction of the heat shock response in hemolymph of M. edulis exposed to tributyltin and copper. Samples were exposed invitro to the concentrations indicated and then incubated for four hours in 35-S methionine. Samples were processed as described in FIG. 5. Arrows at the left are for the molecular weight markers. Those on the right indicate stress proteins of approximately 110, 85, 78, 74, 72, 60, 38, 36 and 27 kDa, respectively. TBT=tributyltin, ppt=parts per trillion, pCu=−log of free cupric ion concentration. Lane 12 involved an unpolluted concentration of stressor. Lanes 8-11 involved polluted concentrations of stressor, with lane 8 involving an acute level.

Figure 8:
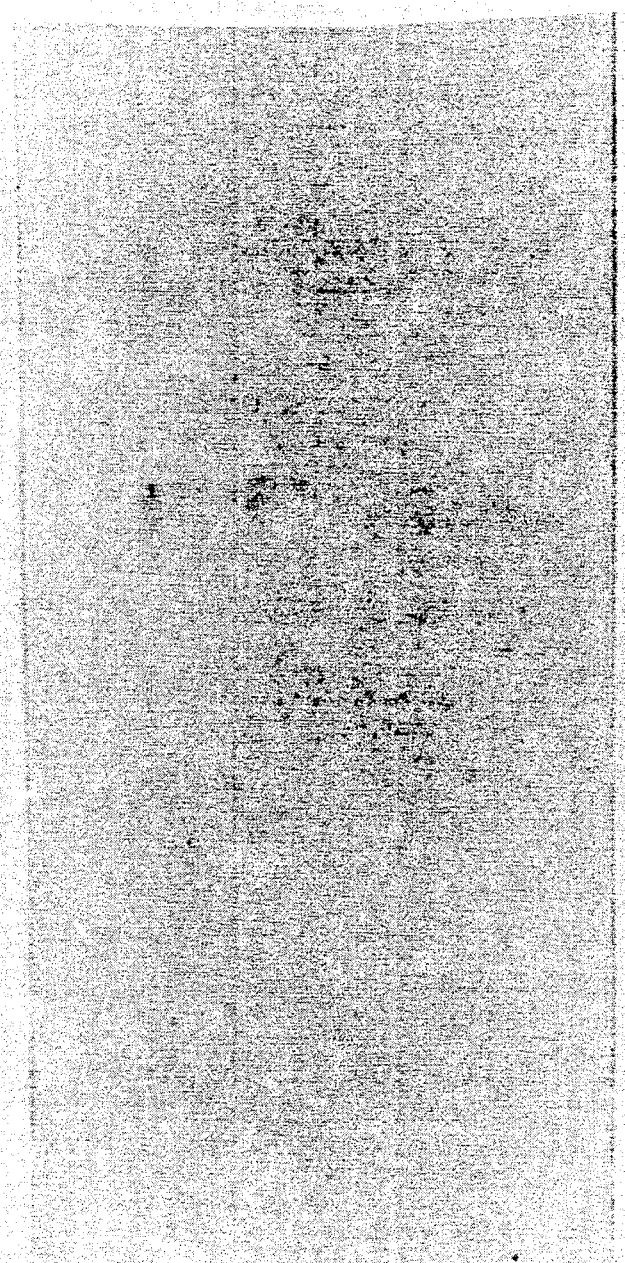
FIG. 8 is a Western blot of *M. edulis* mantel tissue against a monoclonal antibody raised against mammalian hsp 70 (from W. Welch).

FIG. 8 is a Western blot of M. edulis mantle tissue against a monoclonal antibody raised against mamallian hsp 70 (from W. Welch). Tissues were exposed or 8 hours in vitro to copper, tributyltin, heat shock for 1 hour at 31° C. and a 17° C. control sample, from left to right, respectively. Samples of equal protein were run on a 12% SDS gel before blotting. Arrows at the right designate prestained markets of approximately 194, 111 and 60 kDa, respectively. Cu=copper exposed sample, TBT=tributyltin exposed sample, HS=heat shock at 31° C., C=control.

Figure 9:
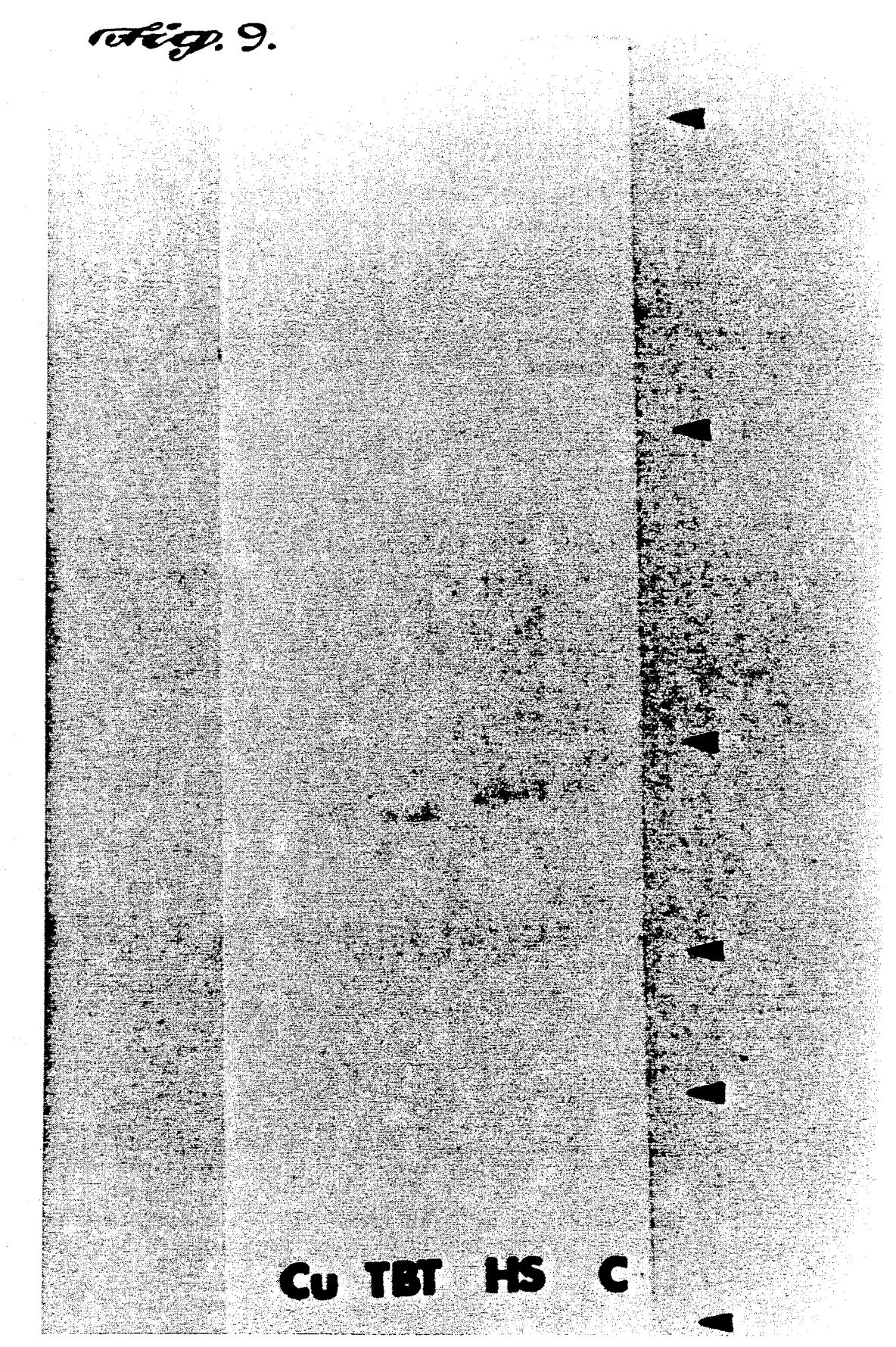

FIG. 9 is a Western blot of M. edulis mantle tissue against a monoclonal antibody raised against hsp 60 in moth. Tissues and electrophoresis are described in FIG. 8. Arrows represent prestained markers of approximately 194, 111, 60, 35, 26, 20 and 16 kDa, respectively. C=copper exposed sample, TBT=tributyltin exposed sample, HS=heat shock at 31° C., C=control.

The Gene Probe Technology

This aspect of the present invention is based on the increase in mRNA levels during the heat shock response. It should be noted that measuring hsp mRNA levels will probably not work in chronic situations; however, assays for increased levels of hsp mRNA's using gene probes may be useful for detecting acute and/or transient heat shock response, and may be involved in diagnostic procedures, for example.

The stress response entails a major redirection of the activities of the cell. The mRNA population of the cell that existed prior to stress shows a major decrease in its ability to direct peptide synthesis, as a consequence of increased degradation and decreased synthesis. On the other hand, new mRNA species, specific for the synthesis of the stress peptides, show quantitative increases of greater than 20-fold for individual species. This marked increase in the level of specific RNA sequences can be measured by chemically synthesizing an oligonucleotide or gene probe that will specifically hybridize (base-pair) with a particular sequence of the mRNA. The gene probe will typically have attached to it a detectable marker so that the amount of it that is hybridized will reflect the amount of stress-specific mRNA in the cell. Thus, an increase in the binding of the gene probe above normal base levels characteristic of the organism will provide an indication of both environmental stress and its relative severity. In the medical and veterinary assay embodiments, stress peptide detection may be used as an indicator of viral infection or, in the case of isolated organs and tissues, as an indicator of their suitability for transplantation.

By "specifically hybridize," as used herein, it is meant that the subject probes are capable of hybridizing with the mRNA transcribed from the gene for the stress peptide at a stringency condition where a selected number of base-pair mismatches results in nonhybridization. Those skilled in the art will recognize that the stringency conditions for various hybridization assay formats depend upon the constellation of temperature, ionic concentration, and pH. Generally, for optimal RNA:RNA hybridization, the temperature is inversely related to the salt concentration; the pH should be held, e.g., for 15 nucleotide sequences (15-mer), in the range of from about 6.8 to about 7.4. For RNA:DNA hybridizations, similar assay conditions apply, but lower temperatures (accompanied by higher salt concentrations) are generally employed than for RNA:RNA hybridizations.

The gene probe will function in a manner analogous to a lock and key. The gene probe or oligonucleotide can be considered the key and the mRNA that encodes stress peptide the lock. The gene probe is then used to "find" mRNA that cells or tissues by its lock and key interaction. It does this by binding to the mRNA; the more nRNA of the corresponding sequence that is present, the greater will be the amount of gene probe that is bound. The high degree of specificity in the interaction mRNA (lock):gene probe (key) will be ensured by selecting only those regions of the mRNA (nucleotide sequences) that are characteristic of stress-induced mRNAs for detection with the gene probe. Since the complete nucleotide sequences of the mRNAs that specify the stress peptides (e.g., hsp 70, hsp 90) are known for many different organisms, it will be possible to "design" gene probes specific for several different regions of the RNA and to choose the most efficient for a field kit. Human stress peptide amino acid and nucleotide sequences are known, as well as those for several different animals of economic importance. Thus, probes can be designed for use in the present invention to quantitate stress peptide levels for specific medical, veterinary, or industrial uses. Messenger RNA's for any of the hsp's (hsp 60, hsp 70, hsp 90, ubiquitin, and/or low molecular weight hsps) may yield valuable information.

Gene Probe Synthesis

Seventeen to twenty-one residue oligonucleotide probes may be synthesized using an oligonucleotide synthesizer. The oligonucleotides corresponding to various amino acid sequences are purified by polyacrylamide gel electrophoresis, and labeled with a marker so that the amount bound to mRNA can be, for example, visually determined by the intensity of color produced.

Representative sequences will be chosen from regions of homology between the low molecular weight stress peptides (see, Ingolia and Craig, PNAS 79:2360-2364 (1982)), the 70S, 80S, and 90S stress peptide families. Examples of such sequences include:

(1) low molecular weight sequences:

hsp 27: 5'-GAG GGG AAG CAC GAG GAG CGC (representing sense strand amino acid residues 119-125); and hsp 27: 5'-CGT CAC TTT GTG CGC AAG TAT (representing sense strand amino acid residues 135-141)

(2) α-crystalline sequences exhibiting regions of homology with other low molecular weight stress peptides.

Another aspect of the present invention relates to medical diagnosis and screening. Presently, blood banks and other medical facilities rely on personal disclosure of a donor together with biochemical tests for specific infectious agents, such as HIV-I (AIDS) or hepatitis, for screening procedures. The difficulty with this approach in assuring blood quality is that an individual could have become infected immediately prior to donating blood or could have a persistent or latent viral infection where the viral antigens are either not being expressed or only a subset of viral antigens is being expressed. In these situations, antibody-based immunoassays are less likely to "find" sufficient antibodies to elicit positive reactions. Because of the rapid response of cells to stress, stress peptide may signal a stress condition before viral antigens become detectable. Similarly, infected cells may synthesize stress peptides upon infection, even if viral replication is not apparent using standard laboratory antigen-detection systems.

The examples described above are merely exemplary of the use of the present invention. Variations in the actual processes described in the examples will be apparent to those skilled in the art. Therefore, the present invention is to be considered limited only by the appended claims.

The embodiments of the invention in which an exclusive property or privilege is claimed are defined as follows:

1. A method of detecting chronic exposure of an organism to sublethal levels of one or more pollutants in its habitat, comprising:

(a) sampling by removing at least one organism from said habitat under sampling conditions that do not induce a heat shock protein response in said organism;

(b) obtaining a physiological sample of said organisms;

(c) measuring the accumulated concentration in said sample of at least one heat shock protein selected from the group constituting of hsp 70, hsp 60, and ubiquitin;

comparing the heat shock protein concentrations measured in the first and second assays and considering said habitat to have been chronically exposed to sublethal levels of one or more pollutants if said accumulated concentrations are at least about 2 times above a baseline heat shock protein concentration corresponding to an unpolluted habitat and the measured concentrations do not vary more than about 50% one from the other.

2. The method of claim 1, wherein the time period between said first and second assays is at least about 12 hours.

3. The method of claim 2, wherein the time period between said first and second assays is at least about 24 hours.

4. The method of claim 1, wherein the organisms sampled in the first and second assays are congeneric.

5. The method of claim 4, wherein the sampled organisms are of the same species.

6. The method of claim 4, wherein said organisms are selected from the group consisting of prokaryotes, eukaryotes, algae, and plants.

7. The method of claim 1, wherein said physiological sample comprises cells or body fluid.

8. The method of claim 1, wherein said heat shock protein is hsp 60.

9. The method of claim 1, wherein said heat shock protein is hsp 70.

10. The method of claim 1, wherein said heat shock protein is ubiquitin.

11. The method of claim 1, wherein said measuring is carried out by contacting said sample with an immunologic binding partner capable of preferentially binding with one or more of hsp 70, hsp 60, and ubiquitin, and detecting said bound binding partner.

12. The method of claim 1, which further comprises:

comparing said measured heat shock protein concentrations to a predetermined calibration curve which correlates heat shock protein concentration with physiological impairment of growth or reproductive processes due to chronic exposure to sublethal pollutants.

13. A method of detecting biological damage due to chronic exposure of an organism to a pollutant, comprising:

(a) sampling by removing at least on organism from said habitat under sampling conditions that do not induce a heat shock protein response in said organism;

(b) obtaining a physiological sample of said organism;

(c) measuring the accumulated concentration in said sample of at least one heat shock protein selected from the group consisting of hsp 70, hsp 60, and ubiquitin, comparing the heat shock protein concentrations measured in the first and second assays and considering said habitat to have been chronically exposed to sublethal levels of one or more pollutants if said accumulated concentrations are at least about 2 times above a baseline heat shock protein concentration corresponding to an unpolluted habitat and the measured concentrations do not vary more than about 50% one from the other.

* * * * *